United States Patent
Gupta et al.

(10) Patent No.: US 9,650,683 B2
(45) Date of Patent: May 16, 2017

(54) PRIMER FOR AMPLIFYING FARNESYL PYROPHOSPHATE SYNTHASE FROM MANGO

(71) Applicant: Council of Scientific and Industrial Research, New Delhi (IN)

(72) Inventors: Vidya Shrikant Gupta, Pune (IN); Ram Shridhar Kulkarni, Pune (IN); Sagar Subhash Pandit, Pune (IN); Ashok Prabhakar Giri, Pune (IN); Keshav H. Pujari, Dapoli (IN)

(73) Assignee: Council of Scientific and Industrial Research, New Delhi (IN)

( * ) Notice: Subject to any disclaimer, the term of this patent is extended or adjusted under 35 U.S.C. 154(b) by 206 days.

(21) Appl. No.: 14/376,402

(22) PCT Filed: Feb. 1, 2013

(86) PCT No.: PCT/IN2013/000071
§ 371 (c)(1),
(2) Date: Aug. 1, 2014

(87) PCT Pub. No.: WO2013/114406
PCT Pub. Date: Aug. 8, 2013

(65) Prior Publication Data
US 2015/0119562 A1   Apr. 30, 2015

(30) Foreign Application Priority Data
Feb. 3, 2012 (IN) .............................. 0303DEL2012

(51) Int. Cl.
*C12Q 1/68* (2006.01)
*C12N 9/10* (2006.01)

(52) U.S. Cl.
CPC ......... *C12Q 1/6895* (2013.01); *C12N 9/1085* (2013.01); *C12Q 2600/13* (2013.01); *C12Q 2600/158* (2013.01)

(58) Field of Classification Search
None
See application file for complete search history.

(56) References Cited

FOREIGN PATENT DOCUMENTS

WO    WO-2013/114406    8/2013

OTHER PUBLICATIONS

Cane DE, Ikeda H. Exploration and mining of the bacterial terpenome. Acc Chem. Res. Mar. 20, 2012; 45(3):463-72. Epub Oct. 31, 2011. Review.*
Dhar MK, Koul A, Kaul S. Farnesyl pyrophosphate synthase: a key enzyme in isoprenoid biosynthetic pathway and potential molecular target for drug development. N Biotechnol. Jan. 25, 2013; 30(2):114-23. Epub Jul. 25, 2012.*
Kulkarni R, Pandit S, Chidley H, Nagel R, Schmidt A, Gershenzon J, Pujari K, Giri A, Gupta V. Characterization of three novel isoprenyl diphosphate synthases from the terpenoid rich mango fruit. Plant Physiol Biochem. Oct. 2013; 71:121-31. Epub Jul. 16, 2013.*
Liu PL, Wan JN, Guo YP, Ge S, Rao GY. Adaptive evolution of the chrysanthemyl diphosphate synthase gene involved in irregular monoterpene metabolism. BMC Evol Biol. Nov. 8, 2012; 12:214.*
Szkopińska A, Plochocka D. Farnesyl diphosphate synthase; regulation of product specificity. Acta Biochim Pol. 2005; 52(1):45-55. Review.*
Genbank Accession No. JN035296-, Mangifera indica farnesyl pyrophosphate synthase (FPPS) mRNA complete cds (GI: 387134591, submitted by Kulkarni et al. May 27, 2011, retrieved on Jun. 28, 2015 from http://www.ncbi.nlm.nih.gov/nuccore/JN035296).*
Genbank Accession No. JN388916.1-, Mangifera indica farnesyl pyrophosphate synthase (FPPS1) gene, complete cds (GI: 387135419, submitted by Kulkarni et al. Jul. 23, 2011, retrieved on Jun. 28, 2015 from http://www.ncbi.nlm.nih.gov/nuccore/JN035296).*
"International Application No. PCT/IN2013/000071, Article 19 Amendment filed Jan. 6, 2014", (Jan. 6, 2014), 7 pgs.
"International Application No. PCT/IN2013/000071, International Search Report mailed Nov. 5, 2013", (Nov. 5, 2013), 4 pgs.

* cited by examiner

*Primary Examiner* — Samuel Woolwine
*Assistant Examiner* — Olayinka Oyeyemi
(74) *Attorney, Agent, or Firm* — Schwegman Lundberg & Woessner, P.A.

(57) ABSTRACT

The present invention discloses primers for amplifying farnesyl pyrophosphate synthase gene, having sequence selected from the group consisting of Seq Id. nos. 1-3 and 5-7, from mango. Also disclosed herein is a novel nucleotide sequence of sequence ID no. 8 encoding said amplified farnesyl pyrophosphate synthase (FPPS) for enzyme production in an artificial system thus generating the desired flavor in food products.

6 Claims, 5 Drawing Sheets

Figures 2A, 2B:
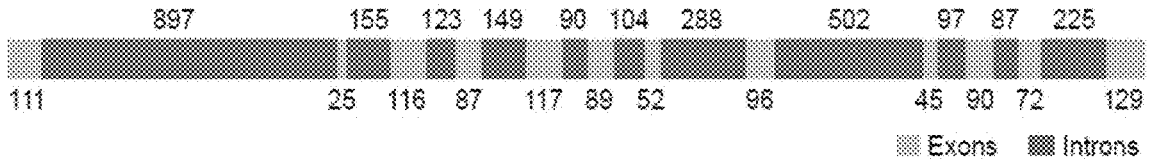

ATGAGTGATTTGAAGTCCAAGTTCGTGGAGGTTTACAATATCTTAAAACAGGAGCTTCTCAATGACCC
TGCCTTTGAATTTACTGACGTTTCTCGCCAATGGGTCGAACGTATGCTGGATTACAATGTTCCTGGAG
GGAAGCTGAACCGAGGGCTTTCTGTTGTTGACAGCTACAAGCTACTGAAAGAAGGGAAGAACTAACA
GATGATGAAATTTTTCTTTCATCTGCACTTGGCTGGTGTATCGAATGGCTTCAGGCTTATTTTCTTGT
TCTTGATGATATCATGGATGGCTCACATACACGTCGTGGTCAACCTGCTGGTTCAGACGTCCGAAGA
TTGGTATGATTGCCGTAAATGATGGCATAATACTTCGCAACCATATCCCAAGAATTTGAAGAAGCAT
TTTAGGGAAAGCCTTATTATGTGGACTTGTTGGATTTATTAATGAGGTCGAATTCAAACAGCTTC
AGGACAAATGATAGACTTAATTACTACAATTGAGGGGGAGAAAGATCTAACAAAGTATTCATTGCCAC
TTCATTGCCAGATAGTTCAGTACAAAACTGCTTATTACTCTTTCTACCTTCCGGTTGCTTGTGCTTTA
CTGATGGCAGGCAAAAATCTTGATGATCACATTGATGTCAAGAACATTCTTATTGAAATGGGAATCTA
TTTTCAAGTACAGGATGATTATCTAGATTGTTTTGGCACTCCTGAAGTGATTGGTAAGATTGGAACTG
ATATTGAAGATTTTAAGTGCTCTTGGTTGGTTGTGAAAGCAATGGAACGTTGTAACGAAGAACAGAAG
AAATTGTTAATTGAGAATTATGGGAAAGCAGATCCAGCCTGTGTTGCAAAGTAAAGAGCTTTACAA
TACTATCGATCTTCAGGGTGCGTTTGCAGAGTATGAAAGTGCAAGTTATGAAAGGTTAATCAAATCCA
TTGAAGCTCATCCCAATAAGGCCATTCAAGCTTTGTTGAAGTCATTTTTAGCCAAGATATATAAGAGG
CAGAAGTAG

FIGURE 1

SEQUENCE LISTING

```
<160> NUMBER OF SEQ ID NOS: 20

<210> SEQ ID NO 1
<211> LENGTH: 22
<212> TYPE: DNA
<213> ORGANISM: Artificial Sequence
<220> FEATURE:
<223> OTHER INFORMATION: A synthetic primer
<220> FEATURE:
<223> OTHER INFORMATION: Degenerate forward primer (1)-FPPS

<400> SEQUENCE: 1
tkgaytacaa ygtvcchgga gg                                          22

<210> SEQ ID NO 2
<211> LENGTH: 23
<212> TYPE: DNA
<213> ORGANISM: Artificial Sequence
<220> FEATURE:
<223> OTHER INFORMATION: A synthetic primer
<220> FEATURE:
<223> OTHER INFORMATION: Degenerate forward primer (2)-FPPS

<400> SEQUENCE: 2
cyctyggytg gygyattgaa tgg                                         23

<210> SEQ ID NO 3
<211> LENGTH: 24
<212> TYPE: DNA
<213> ORGANISM: Artificial Sequence
<220> FEATURE:
<223> OTHER INFORMATION: A synthetic primer
<220> FEATURE:
<223> OTHER INFORMATION: Degenerate Reverse Primer-FPPS
```

```
<400> SEQUENCE: 3
ytayttytgc ctcttrtada tytt                                              24

<210> SEQ ID NO 4
<211> LENGTH: 26
<212> TYPE: DNA
<213> ORGANISM: Artificial Sequence
<220> FEATURE:
<223> OTHER INFORMATION: A synthetic primer
<220> FEATURE:
<223> OTHER INFORMATION: Gene Specific Forward Primer-FPPS

<400> SEQUENCE: 4
agtattcatt gccacttcat tgccag                                            26

<210> SEQ ID NO 5
<211> LENGTH: 25
<212> TYPE: DNA
<213> ORGANISM: Artificial Sequence
<220> FEATURE:
<223> OTHER INFORMATION: A synthetic primer
<220> FEATURE:
<223> OTHER INFORMATION: Gene Specific Reverse Primer-FPPS

<400> SEQUENCE: 5
actttcatac tctgcaaacg caccc                                             25

<210> SEQ ID NO 6
<211> LENGTH: 25
<212> TYPE: DNA
<213> ORGANISM: Artificial Sequence
<220> FEATURE:
<223> OTHER INFORMATION: A synthetic primer
<220> FEATURE:
<223> OTHER INFORMATION: Terminal Forward Primer-FPPS

<400> SEQUENCE: 6
atgagtgatt tgaagtccaa gttcg                                             25

<210> SEQ ID NO 7
<211> LENGTH: 26
<212> TYPE: DNA
<213> ORGANISM: Artificial Sequence
<220> FEATURE:
<223> OTHER INFORMATION: A synthetic primer
<220> FEATURE:
<223> OTHER INFORMATION: Terminal Reverse Primer-FPPS

<400> SEQUENCE: 7
ctacttctgc ctcttatata tcttgg                                            26

<210> SEQ ID NO 8
<211> LENGTH: 1029
<212> TYPE: DNA
<213> ORGANISM: Mangifera indica
<220> FEATURE:
<223> OTHER INFORMATION: Farnesyl pyrophosphate synthase (MiFPPS), mRNA,
      complete cds

<400> SEQUENCE: 8
atgagtgatt tgaagtccaa gttcgtggag gtttacaata tcttaaaaca ggagcttctc       60
aatgaccctg cctttgaatt tactgacgtt tctcgccaat gggtcgaacg tatgctggat      120
tacaatgttc ctggagggaa gctgaaccga gggcttctg ttgttgacag ctacaagcta       180
ctgaaagaag gggaagaact aacagatgat gaaatttttc tttcatctgc acttggctgg      240
```

```
tgtatcgaat ggcttcaggc ttatttctt gttcttgatg atatcatgga tggctcacat    300
acacgtcgtg gtcaaccttg ctggttcaga cgtccgaaga ttggtatgat tgccgtaaat    360
gatggcataa tacttcgcaa ccatatccca agaattttga agaagcattt taggggaaag    420
ccttattatg tggacttgtt ggattatttt aatgaggtcg aatttcaaac agcttcagga    480
caaatgatag acttaattac tacaattgag ggggagaaag atctaacaaa gtattcattg    540
ccacttcatt gccagatagt tcagtacaaa actgcttatt actctttcta ccttccggtt    600
gcttgtgctt tactgatggc aggcaaaaat cttgatgatc acattgatgt caagaacatt    660
cttattgaaa tgggaatcta ttttcaagta caggatgatt atctagattg ttttggcact    720
cctgaagtga ttggtaagat tggaactgat attgaagatt ttaagtgctc ttggttggtt    780
gtgaaagcaa tggaacgttg taacgaagaa cagaagaaat tgttaattga gaattatggg    840
aaagcagatc cagcctgtgt tgcaaaagta aaagagcttt acaatactat cgatcttcag    900
ggtgcgtttg cagagtatga aagtgcaagt tatgaaaggt taatcaaatc cattgaagct    960
catcccaata aggccattca agctttgttg aagtcatttt tagccaagat atataagagg   1020
cagaagtag                                                             1029
```

<210> SEQ ID NO 9
<211> LENGTH: 342
<212> TYPE: PRT
<213> ORGANISM: Artemisia tridentata

<400> SEQUENCE: 9

```
Met Ser Ile Asp Leu Lys Ser Arg Phe Leu Gln Val Tyr Asp Ser Leu
 1               5                  10                  15

Lys Ser Asp Leu Ile His Asp Pro Ala Phe Glu Phe Asp Asp Ser
            20                  25                  30

Arg Asn Trp Val Glu Arg Met Leu Asp Tyr Asn Val Pro Gly Gly Lys
        35                  40                  45

Leu Asn Arg Gly Leu Ser Val Val Asp Ser Tyr Lys Leu Leu Lys Gln
    50                  55                  60

Glu Glu Leu Thr Glu Asp Glu Val Phe Leu Ala Cys Ala Leu Gly Trp
65                  70                  75                  80

Cys Ile Glu Trp Leu Gln Ala Tyr Phe Leu Val Leu Asp Asp Ile Met
                85                  90                  95

Asp Glu Ser His Thr Arg Arg Gly Gln Pro Cys Trp Phe Arg Leu Pro
            100                 105                 110

Lys Val Gly Met Ile Ala Val Asn Asp Gly Val Val Leu Arg Asn His
        115                 120                 125

Ile Pro Arg Ile Leu Lys Lys His Phe Arg Gly Lys Ala Tyr Tyr Ala
    130                 135                 140

Asp Leu Leu Asp Leu Phe Asn Glu Val Glu Phe Gln Thr Ala Ser Gly
145                 150                 155                 160

Gln Met Ile Asp Leu Ile Thr Thr Leu Phe Gly Gln Lys Glu Leu Ser
                165                 170                 175

Lys Tyr Ser Leu Ser Thr His Gln Arg Ile Val Lys Phe Lys Thr Ala
            180                 185                 190

Tyr Tyr Ser Phe Tyr Leu Pro Val Ala Cys Ala Leu Leu Met Phe Gly
        195                 200                 205

Glu Asn Leu Asp Asp His Val Gln Val Lys Asp Val Leu Val Glu Met
    210                 215                 220
```

```
Gly Thr Tyr Phe Gln Val Gln Asp Asp Tyr Leu Asp Cys Phe Gly Ser
225                 230                 235                 240

Pro Glu Val Ile Gly Lys Ile Gly Thr Asp Ile Glu Asp Phe Lys Cys
                245                 250                 255

Ser Trp Leu Val Val Lys Ala Leu Glu Leu Ala Asp Glu Gln Gln Lys
            260                 265                 270

Lys Leu Leu Asn Glu Asn Tyr Gly Arg Lys Asp Pro Ala Ser Val Ala
        275                 280                 285

Lys Val Lys Glu Leu Tyr His Thr Leu Asn Leu Gln Gly Val Phe Glu
    290                 295                 300

Asp Tyr Glu Asn Lys Ser His Glu Lys Ile Ile Lys Ser Ile Glu Thr
305                 310                 315                 320

His Pro Ser Lys Ala Val Gln Glu Val Leu Lys Ser Phe Leu Gly Lys
                325                 330                 335

Ile Phe Lys Arg Gln Lys
                340

<210> SEQ ID NO 10
<211> LENGTH: 342
<212> TYPE: PRT
<213> ORGANISM: Canellaasiattca

<400> SEQUENCE: 10

Met Ser Asp Leu Lys Thr Arg Phe Leu Glu Val Tyr Ser Val Leu Lys
1               5                   10                  15

Ser Asp Leu Leu Asn Asp Pro Ala Phe Glu Phe Thr Asp Asp Ser Arg
            20                  25                  30

Gln Trp Val Glu Arg Met Leu Asp Tyr Asn Val Pro Gly Gly Lys Leu
        35                  40                  45

Asn Arg Gly Leu Ser Val Ile Asp Ser Tyr Lys Leu Leu Lys Glu Gly
    50                  55                  60

Lys Glu Leu Ser Asp Asp Glu Ile Val Leu Ser Ser Ala Leu Gly Trp
65                  70                  75                  80

Cys Ile Glu Trp Leu Gln Ala Tyr Phe Leu Val Leu Asp Asp Ile Met
                85                  90                  95

Asp Gly Ser His Thr Arg Arg Gly Gln Pro Cys Trp Phe Arg Ile Pro
                100                 105                 110

Lys Val Gly Met Ile Ala Ile Asn Asp Gly Ile Leu Leu Arg Asn His
            115                 120                 125

Ile Pro Arg Ile Leu Lys Lys His Phe Arg Gln Lys Pro Tyr Tyr Val
130                 135                 140

Asp Leu Leu Asp Leu Phe Asn Glu Val Glu Phe Gln Thr Ala Cys Gly
145                 150                 155                 160

Gln Met Ile Asp Leu Ile Thr Thr Leu Val Gly Glu Lys Asp Leu Ser
                165                 170                 175

Lys Tyr Ser Leu Pro Ile His Arg Arg Ile Val Gln Tyr Lys Thr Ala
            180                 185                 190

Tyr Tyr Ser Phe Tyr Leu Pro Val Ala Cys Ala Leu Leu Met Ala Gly
        195                 200                 205

Glu Asp Leu Glu Lys His Thr Asn Val Lys Asp Ile Leu Ile Glu Met
    210                 215                 220

Gly Thr Tyr Phe Gln Val Gln Asp Asp Tyr Leu Asp Cys Phe Gly Ala
225                 230                 235                 240

Pro Glu Val Ile Gly Lys Ile Gly Thr Asp Ile Glu Asp Phe Lys Cys
                245                 250                 255
```

```
Ser Trp Leu Val Val Lys Ala Leu Glu Leu Ser Asn Glu Glu Gln Lys
            260                 265                 270

Lys Cys Leu His Glu Asn Tyr Gly Lys Glu Asp Pro Ala Cys Val Ala
            275                 280                 285

Lys Ile Lys Glu Leu Tyr Lys Asp Leu Lys Leu Gln Asp Val Phe Ala
            290                 295                 300

Glu Tyr Glu Ser Lys Ser Tyr Glu Lys Leu Ile Lys Phe Ile Glu Ala
305                 310                 315                 320

His Pro Asn Gln Ser Val Gln Ala Val Leu Lys Ser Phe Leu Gly Lys
                325                 330                 335

Ile Tyr Lys Arg Gln Lys
            340

<210> SEQ ID NO 11
<211> LENGTH: 390
<212> TYPE: PRT
<213> ORGANISM: Ginko biloba

<400> SEQUENCE: 11

Met Gln Phe Pro Ser Leu Arg Lys Leu His Ser Ile Phe Arg Val Glu
  1               5                  10                  15

Ala Leu Tyr Tyr Gly Ile Gly Leu Ser Gly Arg Glu Ser Thr Ser Lys
             20                  25                  30

Glu Phe Arg Ser Leu His Pro Gly Phe Ala Ala Met Glu Ser Asn Cys
         35                  40                  45

Asn Ala Asn Thr Arg Ser Lys Phe Leu Glu Val Tyr Asn Val Leu Lys
 50                  55                  60

Ser Gln Ile Leu Asn Asp Ser Ala Phe Gln Cys Thr Asp Asp Ala Arg
 65                  70                  75                  80

Gln Trp Ile Glu Lys Met Leu Asp Tyr Thr Val Pro Gly Gly Lys Leu
             85                  90                  95

Asn Arg Gly Leu Ser Val Ile Asp Ser Tyr Arg Leu Leu Lys Thr Gly
            100                 105                 110

Lys Glu Ile Thr Glu Asp Glu Val Phe Leu Gly Cys Val Leu Gly Trp
            115                 120                 125

Cys Ile Glu Trp Leu Gln Ala Tyr Phe Leu Val Leu Asp Asp Ile Met
            130                 135                 140

Asp Gly Ser His Thr Arg Arg Gly Gln Pro Cys Trp Phe Arg Leu Pro
145                 150                 155                 160

Gln Val Gly Leu Ile Ala Ala Asn Asp Gly Ile Leu Leu Arg Thr His
            165                 170                 175

Ile Ser Arg Ile Leu Lys Leu His Phe Gln Thr Lys Pro Tyr Tyr Val
            180                 185                 190

Asp Leu Cys Asp Leu Phe Asn Glu Val Glu Phe Gln Thr Ala Ser Gly
            195                 200                 205

Gln Met Leu Asp Leu Ile Thr Thr His Glu Gly Ala Ile Asp Leu Ala
            210                 215                 220

Lys Tyr Lys Met Pro Thr Tyr Leu Arg Ile Val Gln Tyr Lys Thr Ala
225                 230                 235                 240

Tyr Tyr Ser Phe Tyr Leu Pro Val Ala Cys Ala Leu Leu Met Ala Gly
            245                 250                 255

Glu Asn Leu Asp Asn Phe Val Ala Val Lys Asn Ile Leu Val Gln Met
            260                 265                 270

Gly Thr Tyr Phe Gln Val Gln Asp Asp Tyr Leu Asp Cys Phe Gly Asp
```

```
            275                 280                 285
Pro Glu Val Ile Gly Lys Ile Gly Thr Asp Ile Glu Asp Phe Lys Cys
    290                 295                 300

Ser Trp Leu Ile Val Gln Ala Leu Glu Arg Ala Asn Glu Ser Gln Arg
305                 310                 315                 320

Lys Gln Leu Tyr Asp Asn Tyr Gly Lys Ala Asp Pro Ser Cys Val Ala
                325                 330                 335

Ala Val Lys Ala Ile Tyr Arg Asp Leu Gly Ile Gln Asp Ile Phe Leu
            340                 345                 350

Glu Tyr Glu Arg Ser Ser His Lys Glu Leu Ile Ser Ser Ile Glu Ala
        355                 360                 365

Gln Glu Asn Glu Ser Val Gln Leu Val Leu Lys Ser Phe Leu Gly Lys
    370                 375                 380

Ile Tyr Lys Arg Gln Lys
385                 390

<210> SEQ ID NO 12
<211> LENGTH: 342
<212> TYPE: PRT
<213> ORGANISM: Lupinusalbus

<400> SEQUENCE: 12

Met Ala Asp Leu Arg Ser Thr Phe Leu Asn Val Tyr Ser Val Leu Lys
1               5                   10                  15

Ser Glu Leu Leu His Asp Pro Ala Phe Glu Phe Ser Pro Asp Ser Arg
            20                  25                  30

Gln Trp Leu Asp Arg Met Leu Asp Tyr Asn Val Pro Gly Gly Lys Leu
        35                  40                  45

Asn Arg Gly Leu Ser Val Ile Asp Ser Tyr Arg Leu Leu Lys Asp Gly
    50                  55                  60

His Glu Leu Asn Asp Asp Glu Ile Phe Leu Ala Ser Ala Leu Gly Trp
65                  70                  75                  80

Cys Ile Glu Trp Leu Gln Ala Tyr Phe Leu Val Leu Asp Asp Ile Met
                85                  90                  95

Asp Asn Ser His Thr Arg Arg Gly Gln Pro Cys Trp Phe Arg Val Pro
            100                 105                 110

Lys Val Gly Met Ile Ala Ala Asn Asp Gly Val Leu Leu Arg Asn His
        115                 120                 125

Ile Pro Arg Ile Leu Lys Lys His Phe Arg Gly Lys Pro Tyr Tyr Ala
    130                 135                 140

Asp Leu Leu Asp Leu Phe Asn Glu Val Glu Phe Gln Thr Ala Ser Gly
145                 150                 155                 160

Gln Met Ile Asp Leu Ile Thr Thr Leu Glu Gly Glu Lys Asp Leu Ser
                165                 170                 175

Lys Tyr Thr Leu Ser Leu His Arg Arg Ile Val Gln Tyr Lys Thr Ala
            180                 185                 190

Tyr Tyr Ser Phe Tyr Leu Pro Val Ala Cys Ala Leu Leu Met Val Gly
        195                 200                 205

Glu Asn Leu Asp Asn His Ile Asp Val Lys Asn Ile Leu Val Asp Met
    210                 215                 220

Gly Thr Tyr Phe Gln Val Gln Asp Asp Tyr Leu Asp Cys Phe Gly Ala
225                 230                 235                 240

Pro Glu Thr Ile Gly Lys Ile Gly Thr Asp Ile Glu Asp Phe Lys Cys
                245                 250                 255
```

```
Ser Trp Leu Val Val Lys Ala Leu Glu Leu Ser Asn Asp Glu Gln Lys
            260                 265                 270

Lys Val Leu Tyr Asp Asn Tyr Gly Lys Pro Asp Pro Ala Asn Val Ala
            275                 280                 285

Lys Val Lys Ala Leu Tyr Asp Glu Leu Asn Leu Gln Gly Val Phe Thr
290                 295                 300

Glu Tyr Glu Ser Lys Ser Tyr Glu Lys Leu Val Thr Ser Ile Glu Ala
305                 310                 315                 320

His Pro Ser Lys Ala Val Gln Ala Leu Leu Lys Ser Phe Leu Gly Lys
            325                 330                 335

Ile Tyr Lys Arg Gln Lys
            340

<210> SEQ ID NO 13
<211> LENGTH: 349
<212> TYPE: PRT
<213> ORGANISM: Menth x piperita

<400> SEQUENCE: 13

Met Ala Asn Leu Asn Gly Ala Ala Ser Asp Leu Arg Lys Thr Phe Leu
1               5                   10                  15

Gly Val Tyr Ser Thr Leu Lys Ser Glu Leu Leu Asn Asp Pro Ala Phe
            20                  25                  30

Glu Trp Thr Asp Gly Ser Arg Gln Trp Val Glu Arg Met Leu Asp Tyr
            35                  40                  45

Asn Val Pro Gly Gly Lys Leu Asn Arg Gly Leu Ser Val Ile Asp Ser
    50                  55                  60

Tyr Gln Leu Leu Lys Glu Gly Lys Asp Leu Thr Asp Asp Glu Val Phe
65                  70                  75                  80

Leu Ala Ser Ala Leu Gly Trp Cys Ile Glu Trp Leu Gln Ala Tyr Phe
                85                  90                  95

Leu Val Leu Asp Asp Ile Met Asp Asn Ser His Thr Arg Arg Gly Gln
            100                 105                 110

Pro Cys Trp Phe Lys Val Pro Lys Val Gly Met Ile Ala Ile Asn Asp
            115                 120                 125

Gly Ile Ile Leu Arg Asn His Ile Pro Arg Ile Leu Lys Lys His Phe
130                 135                 140

Arg Ser Lys Pro Tyr Tyr Val Asp Leu Leu Asp Leu Phe Asn Glu Val
145                 150                 155                 160

Glu Phe Gln Thr Ala Ser Gly Gln Met Ile Asp Leu Ile Thr Thr Ile
                165                 170                 175

Glu Gly Glu Lys Asp Leu Ser Lys Tyr Ser Leu Pro Leu His Arg Arg
            180                 185                 190

Ile Val Gln Tyr Lys Thr Ala Tyr Tyr Ser Phe Tyr Leu Pro Val Ala
            195                 200                 205

Cys Ala Leu Leu Met Ala Gly Glu Asn Leu Glu Asn His Pro Thr Val
            210                 215                 220

Lys Asp Val Leu Ile Asp Met Gly Ile Tyr Phe Gln Val Gln Asp Asp
225                 230                 235                 240

Tyr Leu Asp Cys Phe Gly Glu Pro Glu Lys Ile Gly Lys Ile Gly Thr
                245                 250                 255

Asp Ile Glu Asp Phe Lys Cys Ser Trp Leu Val Val Lys Ala Leu Glu
            260                 265                 270

Leu Cys Asn Glu Glu Gln Lys Lys Thr Leu Phe Glu His Tyr Gly Lys
            275                 280                 285
```

```
Glu Asn Pro Ala Asp Val Ala Lys Ile Lys Ala Leu Tyr Asn Asp Ile
    290                 295                 300

Asn Leu Gln Gly Met Phe Ala Asp Phe Glu Ser Lys Ser Tyr Glu Lys
305                 310                 315                 320

Ile Thr Ser Ser Ile Glu Ala His Pro Ser Lys Ser Val Gln Ala Val
                325                 330                 335

Leu Lys Ser Phe Leu Gly Lys Ile Tyr Lys Arg Gln Lys
            340                 345

<210> SEQ ID NO 14
<211> LENGTH: 342
<212> TYPE: PRT
<213> ORGANISM: Panax ginseng

<400> SEQUENCE: 14

Met Ser Asp Leu Lys Thr Arg Phe Leu Glu Val Tyr Ser Val Leu Lys
1               5                   10                  15

Ser Glu Leu Leu Asn Asp Pro Ala Phe Glu Phe Thr Asp Asp Ser Arg
            20                  25                  30

Gln Trp Val Glu Arg Met Leu Asp Tyr Asn Val Pro Gly Gly Lys Leu
        35                  40                  45

Asn Arg Gly Leu Ser Val Ile Asp Ser Tyr Lys Leu Leu Lys Glu Gly
    50                  55                  60

Lys Glu Leu Ser Asp Asp Glu Ile Phe Leu Ser Ser Ala Leu Gly Trp
65                  70                  75                  80

Cys Ile Glu Trp Leu Gln Ala Tyr Phe Leu Val Leu Asp Asp Ile Met
                85                  90                  95

Asp Ser Ser His Thr Arg Arg Gly Gln Pro Cys Trp Phe Arg Leu Pro
            100                 105                 110

Lys Val Gly Met Ile Ala Val Asn Asp Gly Ile Leu Leu Arg Asn His
        115                 120                 125

Ile Pro Arg Ile Leu Lys Lys His Phe Arg Gln Lys Pro Tyr Tyr Val
    130                 135                 140

Asp Leu Leu Asp Leu Phe Asn Glu Val Glu Phe Gln Thr Ala Ser Gly
145                 150                 155                 160

Gln Met Ile Asp Leu Ile Thr Thr Leu Val Gly Glu Lys Asp Leu Ser
                165                 170                 175

Lys Tyr Ser Leu Pro Ile His Arg Arg Ile Val Gln Tyr Lys Thr Ala
            180                 185                 190

Tyr Tyr Ser Phe Tyr Leu Pro Val Ala Cys Ala Leu Leu Met Ser Gly
        195                 200                 205

Glu Asp Leu Glu Lys His Thr Asn Val Lys Asp Ile Leu Ile Glu Met
    210                 215                 220

Gly Thr Tyr Phe Gln Val Gln Asp Asp Tyr Leu Asp Cys Phe Gly Ala
225                 230                 235                 240

Pro Glu Val Ile Gly Lys Ile Gly Thr Asp Ile Glu Asp Phe Lys Cys
                245                 250                 255

Ser Trp Leu Val Val Lys Ala Leu Glu Leu Ser Asn Glu Glu Gln Lys
            260                 265                 270

Lys Phe Leu His Glu Asn Tyr Gly Lys Asp Asp Pro Ala Ser Val Ala
        275                 280                 285

Lys Val Lys Glu Leu Tyr Asn Thr Leu Lys Leu Gln Asp Val Phe Ala
    290                 295                 300

Glu Tyr Glu Ser Lys Ser Tyr Asp Lys Leu Ile Lys Phe Ile Glu Ala
```

His Pro Ser Gln Ala Val Gln Ala Val Leu Lys Ser Phe Leu Gly Lys
305                 310                 315                 320

Ile Tyr Lys Arg Gln Lys
            325

<210> SEQ ID NO 15
<211> LENGTH: 351
<212> TYPE: PRT
<213> ORGANISM: Taxus x media

<400> SEQUENCE: 15

Met Asp Ser Asn Gly Asn Ala Asn Phe Ser Val Asp Met Lys Ser Lys
1               5                   10                  15

Phe Leu Gln Val Tyr Glu His Leu Lys Ala Glu Ile Leu Arg Asp Pro
            20                  25                  30

Ala Phe Asp Tyr Thr Glu Asp Ala Arg Val Trp Val Glu Lys Met Leu
        35                  40                  45

Asp Tyr Asn Val Pro Gly Gly Lys Leu Asn Arg Gly Leu Ser Val Ile
    50                  55                  60

Asp Ser Tyr Arg Leu Leu Lys Asn Gly Lys Val Leu Ser Glu Gly Glu
65                  70                  75                  80

Val Phe Leu Gly Cys Val Leu Gly Trp Cys Ile Glu Trp Leu Gln Ala
                85                  90                  95

Tyr Phe Leu Val Leu Asp Asp Ile Met Asp Gly Ser His Thr Arg Arg
            100                 105                 110

Gly Gln Pro Cys Trp Phe Arg Leu Pro Lys Val Gly Leu Val Ala Ala
        115                 120                 125

Asn Asp Gly Ile Leu Leu Arg Asn His Ile Thr Arg Ile Leu Lys Met
    130                 135                 140

His Phe Arg Thr Lys Pro Tyr Tyr Ser Asp Pro Leu Asp Leu Phe Asn
145                 150                 155                 160

Glu Val Glu Phe Gln Thr Ala Cys Gly Gln Leu Leu Asp Leu Ile Thr
                165                 170                 175

Thr His Glu Gly Ala Met Asp Leu Ser Lys Tyr Lys Met Pro Thr Tyr
            180                 185                 190

Leu Arg Ile Val Gln Tyr Lys Thr Ala Tyr Tyr Ser Phe Tyr Leu Pro
        195                 200                 205

Val Ala Cys Ala Leu Leu Met Ala Gly Glu Asn Leu Asp Asn Phe Val
    210                 215                 220

Asp Val Lys Asn Ile Leu Ile Gln Met Gly Thr Tyr Phe Gln Val Gln
225                 230                 235                 240

Asp Asp Tyr Leu Asp Cys Phe Gly Asp Pro Gln Val Ile Gly Lys Ile
                245                 250                 255

Gly Thr Asp Ile Glu Asp Phe Lys Cys Ser Trp Leu Val Val Gln Ala
            260                 265                 270

Leu Glu Gln Ala Asn Glu Ser Gln Ile Gln Thr Leu Tyr Ala Asn Tyr
        275                 280                 285

Gly Lys Ala Asp Ser Ser Cys Val Ala Glu Val Lys Ala Leu Tyr Arg
    290                 295                 300

Asp Leu Gly Leu Glu Asp Val Phe Leu Glu Tyr Glu Asn Thr Ser His
305                 310                 315                 320

Lys Asp Leu Ile Ser Ser Ile Glu Ala Gln Lys Glu Ser Val Gln
                325                 330                 335

```
Leu Val Leu Lys Ser Phe Leu Glu Lys Ile Tyr Lys Arg Gln Lys
            340                 345                 350
```

<210> SEQ ID NO 16
<211> LENGTH: 350
<212> TYPE: PRT
<213> ORGANISM: Zea mays

<400> SEQUENCE: 16

```
Met Ala Ala Gly Gly Asn Gly Ala Gly Gly Asp Thr Arg Ala Ala Phe
 1               5                  10                  15

Ala Arg Ile Tyr Lys Thr Leu Lys Glu Glu Leu Leu Thr Asp Pro Ala
            20                  25                  30

Phe Glu Phe Thr Glu Glu Ser Arg Gln Trp Ile Asp Arg Met Val Asp
        35                  40                  45

Tyr Asn Val Leu Gly Gly Lys Cys Asn Arg Gly Leu Ser Val Val Asp
    50                  55                  60

Ser Tyr Lys Leu Leu Lys Gly Ala Asp Ala Leu Gly Glu Glu Glu Thr
65                  70                  75                  80

Phe Leu Ala Cys Thr Leu Gly Trp Cys Ile Glu Trp Leu Gln Ala Phe
                85                  90                  95

Phe Leu Val Leu Asp Asp Ile Met Asp Asp Ser His Thr Arg Arg Gly
            100                 105                 110

Gln Pro Cys Trp Phe Arg Val Pro Gln Val Gly Leu Ile Ala Ala Asn
        115                 120                 125

Asp Gly Ile Ile Leu Arg Asn His Ile Ser Arg Ile Leu Arg Arg His
    130                 135                 140

Phe Lys Gly Lys Pro Tyr Tyr Ala Asp Leu Leu Asp Leu Phe Asn Glu
145                 150                 155                 160

Val Glu Phe Lys Thr Ala Ser Gly Gln Leu Leu Asp Leu Ile Thr Thr
                165                 170                 175

His Glu Gly Glu Lys Asp Leu Thr Lys Tyr Asn Ile Thr Val His Gly
            180                 185                 190

Arg Ile Val Gln Tyr Lys Thr Ala Tyr Tyr Ser Phe Tyr Leu Pro Val
        195                 200                 205

Ala Cys Ala Leu Leu Leu Ser Gly Glu Asn Leu Asp Asn Tyr Gly Asp
    210                 215                 220

Val Glu Asn Ile Leu Val Glu Met Gly Thr Tyr Phe Gln Val Gln Asp
225                 230                 235                 240

Asp Tyr Leu Asp Cys Tyr Gly Asp Pro Glu Phe Ile Gly Lys Ile Gly
                245                 250                 255

Thr Asp Ile Glu Asp Tyr Lys Cys Ser Trp Leu Val Val Gln Ala Leu
            260                 265                 270

Glu Arg Ala Asp Glu Ser Gln Lys Arg Ile Leu Phe Glu Asn Tyr Gly
        275                 280                 285

Lys Lys Asp Pro Ala Cys Val Ala Lys Val Lys Asn Leu Tyr Lys Glu
    290                 295                 300

Leu Asp Leu Glu Ala Val Phe Gln Glu Tyr Glu Asn Glu Ser Tyr Lys
305                 310                 315                 320

Lys Leu Ile Ala Asp Ile Glu Ala Gln Pro Ser Ile Ala Val Gln Lys
                325                 330                 335

Val Leu Lys Ser Phe Leu His Lys Ile Tyr Lys Arg Gln Lys
            340                 345                 350
```

<210> SEQ ID NO 17

<211> LENGTH: 347
<212> TYPE: PRT
<213> ORGANISM: Piceaabies

<400> SEQUENCE: 17

Met Ala Ser Asn Gly Ile Val Asp Val Lys Thr Lys Phe Glu Glu Ile
1               5                   10                  15

Tyr Leu Glu Leu Lys Ala Gln Ile Leu Asn Asp Pro Ala Phe Asp Tyr
            20                  25                  30

Thr Glu Asp Ala Arg Gln Trp Val Glu Lys Met Leu Asp Tyr Thr Val
        35                  40                  45

Pro Gly Gly Lys Leu Asn Arg Gly Leu Ser Val Ile Asp Ser Tyr Arg
50                  55                  60

Leu Leu Lys Ala Gly Lys Glu Ile Ser Glu Asp Glu Val Phe Leu Gly
65                  70                  75                  80

Cys Val Leu Gly Trp Cys Ile Glu Trp Leu Gln Ala Tyr Phe Leu Ile
                85                  90                  95

Leu Asp Asp Ile Met Asp Ser Ser His Thr Arg Arg Gly Gln Pro Cys
            100                 105                 110

Trp Phe Arg Leu Pro Lys Val Gly Leu Ile Ala Val Asn Asp Gly Ile
        115                 120                 125

Leu Leu Arg Asn His Ile Cys Arg Ile Leu Lys Lys His Phe Arg Thr
130                 135                 140

Lys Pro Tyr Tyr Val Asp Leu Leu Asp Leu Phe Asn Glu Val Glu Phe
145                 150                 155                 160

Gln Thr Ala Ser Gly Gln Leu Leu Asp Leu Ile Thr Thr His Glu Gly
                165                 170                 175

Ala Thr Asp Leu Ser Lys Tyr Lys Met Pro Thr Tyr Val Arg Ile Val
            180                 185                 190

Gln Tyr Lys Thr Ala Tyr Tyr Ser Phe Tyr Leu Pro Val Ala Cys Ala
        195                 200                 205

Leu Val Met Ala Gly Glu Asn Leu Asp Asn His Val Asp Val Lys Asn
210                 215                 220

Ile Leu Val Glu Met Gly Thr Tyr Phe Gln Val Gln Asp Asp Tyr Leu
225                 230                 235                 240

Asp Cys Phe Gly Asp Pro Glu Val Ile Gly Lys Ile Gly Thr Asp Ile
                245                 250                 255

Glu Asp Phe Lys Cys Ser Trp Leu Val Val Gln Ala Leu Glu Arg Ala
            260                 265                 270

Asn Glu Ser Gln Leu Gln Arg Leu Tyr Ala Asn Tyr Gly Lys Lys Asp
        275                 280                 285

Pro Ser Cys Val Ala Glu Val Lys Ala Val Tyr Arg Asp Leu Gly Leu
290                 295                 300

Gln Asp Val Phe Leu Glu Tyr Glu Arg Thr Ser His Lys Glu Leu Ile
305                 310                 315                 320

Ser Ser Ile Glu Ala Gln Glu Asn Glu Ser Leu Gln Leu Val Leu Lys
                325                 330                 335

Ser Phe Leu Gly Lys Ile Tyr Lys Arg Gln Lys
            340                 345

<210> SEQ ID NO 18
<211> LENGTH: 342
<212> TYPE: PRT
<213> ORGANISM: Mango

<400> SEQUENCE: 18

Met Ser Asp Leu Lys Ser Lys Phe Val Glu Val Tyr Asn Ile Leu Lys
1               5                   10                  15

Gln Glu Leu Leu Asn Asp Pro Ala Phe Glu Phe Thr Asp Val Ser Arg
            20                  25                  30

Gln Trp Val Glu Arg Met Leu Asp Tyr Asn Val Pro Gly Gly Lys Leu
        35                  40                  45

Asn Arg Gly Leu Ser Val Val Asp Ser Tyr Lys Leu Leu Lys Glu Gly
    50                  55                  60

Glu Glu Leu Thr Asp Asp Glu Ile Phe Leu Ser Ser Ala Leu Gly Trp
65              70                  75                  80

Cys Ile Glu Trp Leu Gln Ala Tyr Phe Leu Val Leu Asp Asp Ile Met
            85                  90                  95

Asp Gly Ser His Thr Arg Arg Gly Gln Pro Cys Trp Phe Arg Arg Pro
            100                 105                 110

Lys Ile Gly Met Ile Ala Val Asn Asp Gly Ile Ile Leu Arg Asn His
            115                 120                 125

Ile Pro Arg Ile Leu Lys Lys His Phe Arg Gly Lys Pro Tyr Tyr Val
    130                 135                 140

Asp Leu Leu Asp Leu Phe Asn Glu Val Glu Phe Gln Thr Ala Ser Gly
145                 150                 155                 160

Gln Met Ile Asp Leu Ile Thr Thr Ile Glu Gly Glu Lys Asp Leu Thr
            165                 170                 175

Lys Tyr Ser Leu Pro Leu His Cys Gln Ile Val Gln Tyr Lys Thr Ala
            180                 185                 190

Tyr Tyr Ser Phe Tyr Leu Pro Val Ala Cys Ala Leu Leu Met Ala Gly
            195                 200                 205

Lys Asn Leu Asp Asp His Ile Asp Val Lys Asn Ile Leu Ile Glu Met
    210                 215                 220

Gly Ile Tyr Phe Gln Val Gln Asp Asp Tyr Leu Asp Cys Phe Gly Thr
225                 230                 235                 240

Pro Glu Val Ile Gly Lys Ile Gly Thr Asp Ile Glu Asp Phe Lys Cys
            245                 250                 255

Ser Trp Leu Val Val Lys Ala Met Glu Arg Cys Asn Glu Glu Gln Lys
            260                 265                 270

Lys Leu Leu Ile Glu Asn Tyr Gly Lys Ala Asp Pro Ala Cys Val Ala
            275                 280                 285

Lys Val Lys Glu Leu Tyr Asn Thr Ile Asp Leu Gln Gly Ala Phe Ala
    290                 295                 300

Glu Tyr Glu Ser Ala Ser Tyr Glu Lys Leu Ile Lys Ser Ile Glu Ala
305                 310                 315                 320

His Pro Asn Lys Ala Ile Gln Ala Leu Leu Lys Ser Phe Leu Ala Lys
            325                 330                 335

Ile Tyr Lys Arg Gln Lys
            340

<210> SEQ ID NO 19
<211> LENGTH: 24
<212> TYPE: DNA
<213> ORGANISM: Artificial Sequence
<220> FEATURE:
<223> OTHER INFORMATION: A synthetic primer

<400> SEQUENCE: 19
tgggaaagca gatccagcct gtgt                                        24

```
<210> SEQ ID NO 20
<211> LENGTH: 25
<212> TYPE: DNA
<213> ORGANISM: Artificial Sequence
<220> FEATURE:
<223> OTHER INFORMATION: A synthetic primer

<400> SEQUENCE: 20
tgcactttca tactctgcaa acgca                                              25
```

PRIMER FOR AMPLIFYING FARNESYL PYROPHOSPHATE SYNTHASE FROM MANGO

PRIORITY CLAIM TO RELATED APPLICATIONS

This application is a U.S. national stage application filed under 35 U.S.C. §371 from International Application Serial No. PCT/IN2013/000071, which was filed Feb. 1, 2013, and published as WO 2013/114406 on Aug. 8, 2013, and which claims priority to India Application No. 0303/DEL/2012, filed Feb. 3, 2012, which applications and publication are incorporated by reference as if reproduced herein and made a part hereof in their entirety, and the benefit of priority of each of which is claimed herein.

FIELD OF THE INVENTION

The present invention relates to primers for amplifying farnesyl pyrophosphate synthase gene from mango. The invention further relates to a nucleotide sequence encoding said amplified Farnesyl Pyrophosphate Synthase (FPPS) for enzyme production in an artificial system thus generating the desired flavor in food products.

BACKGROUND OF THE INVENTION

Terpenoids form the largest class of plant secondary metabolites, comprising more than 55000 compounds. These molecules play very important ecological and physiological functions in plant life including attraction of pollinators, seed disseminators and predators of herbivores, repulsion of herbivores and pathogens, photosynthetic pigments, protein management (prenylation and ubiquitination) and growth regulation (gibberellins) (Vandermoten et al., 2009). In spite of such vast diversity in structure and function, all the terpenoids are derived from the common C5 precursors: dimethylallyl pyrophosphate (DMAPP) and isopentenyl pyrophosphate (IPP). These two building blocks are condensed together by a group of enzymes known as isoprenyldiphosphate synthases or short-chain prenyltransferases. Addition of one molecule of IPP to DMAPP yields geranyl pyrophosphate (GPP, C10). Sequential addition of two IPP units to DMAPP results in the production of farnesyl pyrophosphate (FPP, C15); whereas, addition of three IPP molecules to DMAPP yields geranylgeranyl pyrophosphate (GGPP, C20) (Vandermoten et al., 2009). These prenyl pyrophosphates formed by isoprenyldiphosphate synthases are the substrates in turn for terpene synthases, which produce the parent carbon skeletons of the terpenes. Being rich in the terpene flavorants, mango forms an appropriate system to study biosynthesis and regulation of monoterpenes. Farnesyl pyrophosphate synthase (FPPS) is one of the central enzymes in the terpenoid biosynthetic pathway in mango. The genes encoding FPPS have been isolated and characterized from several plant genera such as *Lupinus* (Attucci et al., 1995), *Parthenium* (Pan et al., 1996), *Oryza* (Sanmiya et al., 1997), *Lycopersicon* (Gaffe et al., 2000; Sallaud et al., 2009) *Ginkgo* (Wang et al., 2004), *Centella* (Kim et al., 2005), *Taxus* (Liao et al., 2006), *Picea* (Schmidt and Gershenzon, 2007), *Chimonanthus* (Xiang et al., 2010) and *Panax* (Kim et al., 2010). The most intensive work on FPPS has been carried out with *Arabidopsis* (Cunillera et al., 1996; Cunillera et al., 1997, 2000; Delourme et al., 1994), (Masferrer et al., 2002) (Closa et al., 2010; Manzano et al., 2006) and *Artemisia* (Chen et al., 2000) (Han et al., 2006) (Hemmerlin et al., 2003) (Matsushita et al., 1996) (Banyai et al., 2010) (Zhao et al., 2003). These and other studies provide evidence on the importance of FPPS in providing the precursor (FPP) for sesquiterpene volatiles and also for the higher terpenoids such as dolichols, phytoalexins, sterols, ubiquinones, farnesylated proteins and prenylatedheme group of cytochrome a and a3 (Chappell, 1995; Weinstein et al., 1986). FPP also contributes to the biosynthesis of carotenoids, chlorophylls, tocopherols, gibberellins and geranylgeranylated proteins, when it is involved in the formation of GGPP (Szkopinska and Plochocka, 2005). In fruit, which produces the whole range of these compounds, FPPS could well acts as a key regulatory point in terpenoid biosynthesis as well as an important player in controlling cell cycle progression, growth, development and general metabolism (Chappell, 1995; Gaffe et al., 2000; Grunter et al., 1994). Being such an important component of fruit physiology and metabolism, it has been hypothesized that FPPS plays a key role in the variable fruit quality that mango (*Mangifera indica* cv. Alphonso) exhibits among' localities (Kulkarni et al., 2012). This hypothesis is based on the fact that such variation is prominently observed in taste, flavor and texture, as well as the color of the fruit, and FPP might affect the development of each of these properties. For example, glycosylated sesquiterpenes contribute to the taste and flavor of fruits, volatile sesquiterpenes to the odor, carotenoids to the color and sterols to the texture (Chappell, 1995; Clark et al., 1987; Seigler, 1998).

Article titled "Farnesyl pyrophosphate synthase from white lupin: molecular cloning, expression, and purification of the expressed protein" by Attucci et. al published in Arch Biochem Biophys. 1995 Aug. 20; 321(2):493-500, discloses the molecular cloning, expression, and purification of Farnesyl pyrophosphate synthase from white lupin. Two full-length cDNA clones (pFPS1 and pFPS2) were isolated and sequenced, and one of them (pFPS2) was expressed in a bacterial system and the enzyme protein encoded by the clone was purified. The deduced amino acid sequence of lupinfarnesyl pyrophosphate synthase pFPS2 shares 90% and 79% identity with those from *Lupinusalbus* (pFPS1) and *Arabidopsis thaliana*, respectively, 51% with the yeast enzyme, and 44% identity with those from rat and human.

Article titled "A cDNA Encoding Farnesyl Pyrophosphate Synthase in White Lupin" by Attucciet. al. published in Plant Physiol. (1995) 108: 835-836 discloses a method of isolating DNA encoding farnesyl pyrophosphate synthase from White Lupin. A λZapIIcDNA library was constructed from poly (A)+ RNA extracted from 10-day-old seedling roots of white lupin (*Lupinusalbus*). A cDNA clone, pFPS1, which contained an insert of 1354 base pairs, was selected and sequenced. The deduced amino acid sequence of the encoded protein has 80% identity with and 90% similarity to that of FPP synthase identified from *A. thaliana* (GenBank accession No. X75789).

Article titled "Cloning and sequencing of a cDNA encoding farnesyl pyrophosphate synthase from *Gossypium arboretum* and its expression pattern in the developing seeds of *Gossypium hirsutum*" by Liu Chang-Jun et. al. published in Acta Botanica Sinica 1998, Volume 40 (8), 703-710, discloses the isolation of a cDNA encoding farnesyl pyrophosphate synthase from *Gossypium arboretum*. Nucleotide sequencing revealed that it is a full length cDNA of 1.28 kb and the putative amino acid sequence exhibited 80.7%, 78.9% and 71.6% identities with the FPP synthases of *Artimisia annua, Arabidopsis thaliana* and *Zea mays* respectively.

U.S. Pat. No. 6,600,094 titled "Recombinant plant expression vector comprising isolated cDNA nucleotide sequence encoding farnesyl pyrophosphate synthase (FPS) derived from seedlings of sunflower (*Helianthus annus*)" reports a process of amplifying and sequencing the sunflower FPS cDNAs by using a pair of universal FPS oligonucleotides probe and then expressing the FPS cDNAs in bacterial cells, carrying out functional complementation assay in yeast mutant to verify its function and generating a line of transgenic tobacco plants, in order to observe the influence of the overexpression of sunflower Farnesyl Pyrophosphate Synthase (SFPS) in vivo.

Article titled 'Expression profiling of various genes during the fruit development and ripening of mango' by Pandit et. al. published in Plant Physiology and Biochemistry, 48 (2010) explores several flavor related genes along with a few associated to the physiology of developing and ripening in 'Alphonso' mango. The temporal and spatial regulation of the genes during development and ripening of 'Alphonso' mango has been analysed. Genes implicated in terpenoid metabolism include geranyl pyrophosphate synthase and geranylgeranyl pyrophosphate synthase.

As seen from the above disclosures, isolation of farnesyl pyrophosphate synthase (FPPS) which plays an important role in the terpenoid biosynthetic pathway and the nucleotide sequence encoding the same, from mango is not known hitherto and there is a long standing need in the prior art for such sequences. Hence the Inventors have attempted in this research to provide artificial sequences which may be used to impart color, flavor and smell as in natural Alphonso mangoes.

OBJECTIVE OF THE INVENTION

It is therefore the object of the present invention to provide primer sequence for amplifying farnesyl pyrophosphate synthase from mango and to provide a novel nucleotide sequence thereof.

SUMMARY OF THE INVENTION

In accordance with the above, the present invention provides primer sequence for amplifying farnesyl pyrophosphate synthase from mango.

In an aspect, the invention provides an isolated nucleotide sequence encoding farnesyl pyrophosphate synthase (FPPS) from mango and a process of isolating the gene encoding functional farnesyl pyrophosphate synthase from mango.

In another aspect of the present invention a novel nucleotide sequence encoding farnesyl pyrophosphate synthase (FPPS) from mango is elucidated which is useful for enzyme production in an artificial system by appropriately mixing with the mango pulp to generate the desired flavor. The nucleotide sequences are also useful in the flavor industry for semi-biosynthesis of flavors via various approaches such as enzyme immobilization, single cell culture, etc., as well as to improve other varieties of mango.

In another embodiment of the present invention primers useful for amplification of farnesyl pyrophosphate synthase gene of mango wherein the said sequence is selected from the group consisting of Seq ID Nos 1-3 and 4-7.

In yet another embodiment the present invention a forward and reverse gene specific primers of FPPS for amplification of the ends of cDNA by rapid amplification of cDNA ends (RACE).

In still another embodiment of the present invention primers corresponding to the terminal regions of the mRNA which are designed for FPPS and which are used for the PCR amplification with mango cDNA as a template are provided.

In yet another embodiment of the present invention methods of biochemical characterization of the FPPS isolated from mango are provided.

BRIEF DESCRIPTION OF THE DRAWINGS & FIGURES

FIG. 1: Complete open reading frame encoding farnesyl pyrophosphate synthase isolated from mango. (Seq ID 8)

FIG. 2: (a) Alignment of MiFPPS with the most similar sequences of other characterized plant FPP synthases. Five regions which are conserved among the isoprenyldiphosphate synthases (I-V) are indicated in dark cyan colour; FARM (region II) and SARM (region V) motifs are indicated in coral colour and the chain length determining stretch in the region II is indicated in purple colour. NCBI accession numbers of the sequences were: AAP74719 (*Artemisia tridentate*; SEQ ID NO:9), AAV58896 (*Centellaasiatica*; SEQ ID NO:10), AAR27053 (*Ginkgo biloba*; SEQ ID NO:11), AAA86687 (*Lupinusalbus*; SEQ ID NO:12), AAK63847 (*Menthaxpiperita*; SEQ ID NO:13), AAY87903 (*Panax ginseng*; SEQ ID NO:14), AAS19931 (*Taxusxmedia*; SEQ ID NO:15), NP_001105039 (*Zea mays*; SEQ ID NO:16) ACA21460 (*Piceaabies*; SEQ ID NO:17) and Mango (SEQ ID NO:18).

(b) Genomic organization of MiFPPS. Numbers on the top and the bottom indicate sizes (base pair) of the introns and the exons, respectively.

Figure 3:
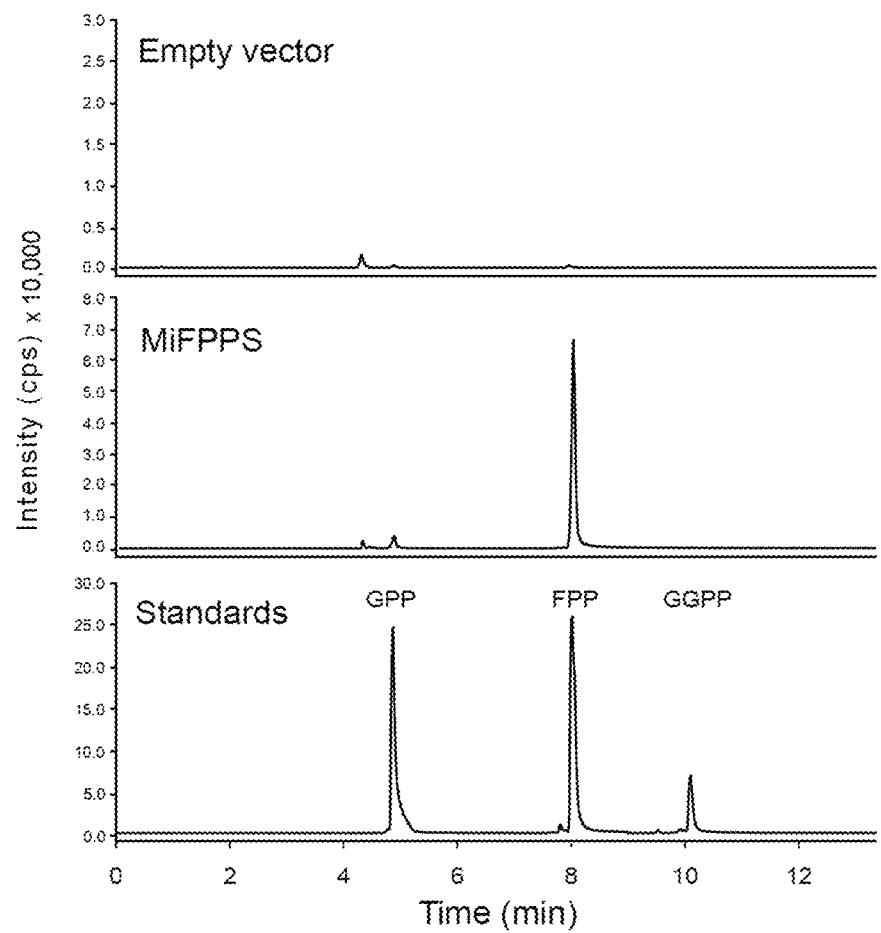

FIG. 3: LC-MS/MS chromatogram of the in vitro assay products formed from IPP and DMAPP with the protein expressed from the empty vector (upper panel), and the purified MiFPPS (middle panel). Chromatogram of standards for GPP, FPP and GGPP is presented in the lower panel.

Figure 4:
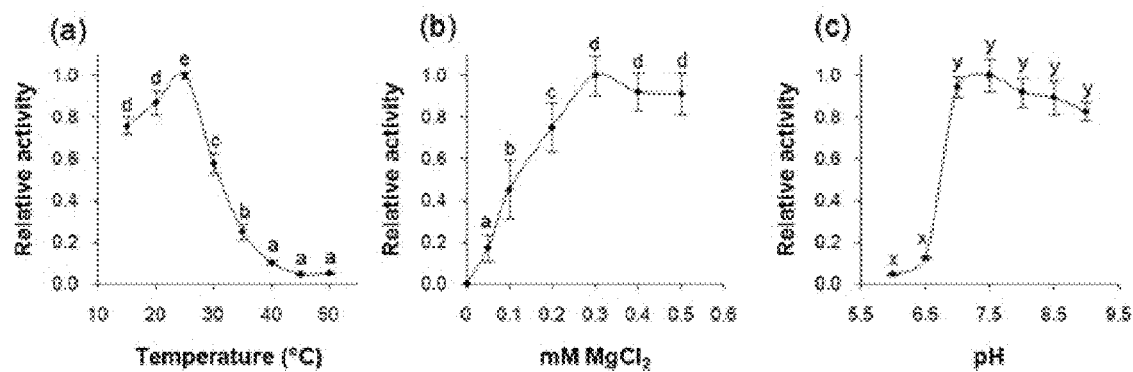

FIG. 4: Optimum temperature, pH and $MgCl_2$ concentration of recombinant MiFPPS. For each parameter, the maximum activity was set to 1. Letters over each point indicate the significance of ANOVA ($p \le 0.05$) carried out by Fisher's LSD test independently for each of the three parameters; the values having different letters are significantly different from each other.

FIG. 5: Homology model of MiFPPS generated using Avian FPPS (IFPS) as a template.

(a) Overall structure of MiFPPS showing the five conserved regions (I-V) in dark cyan colour and FARM and SARM in the region H and V in coral colour. The helical regions have been labelled by the letters A to J; $\alpha$-1, $\alpha$-2 and $\alpha$-3 are the short helices between helices H and I.

(b) Top-view of the model showing central reaction cavity and part of the structure harbouring the residues involved in the catalysis. Side chains of the aspartate residues in the FARM and SARM are indicated in dark cyan colour, those of the other important residues in the conserved regions are shown in coral colour and that of phenylalanine in the chain-length determining region is indicated in green colour.

Figure 6:
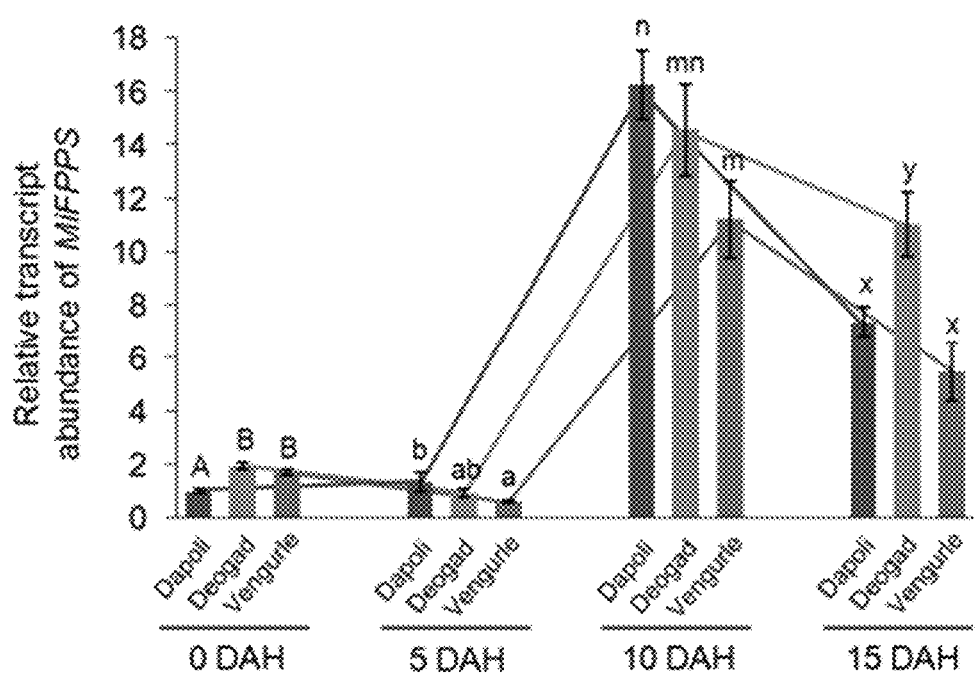

FIG. 6: Abundance of MiFPPS transcripts relative to EF1$\alpha$ during ripening of mango fruits from three cultivation localities, Dapoli, Deogad and Vengurle, in India (DAH: days after harvest). Values presented are averages of four independent biological replicates each of which was represented by at least two technical replicates. Letters over the columns indicate the significance of ANOVA ($p \le 0.05$) carried out by Fisher's LSD test for the comparison between localities for each ripening stages; the values having different letter are significantly different from each other. The ANOVA based comparison is independent for each ripening stage and therefore, is represented by different series of letters (0 DAH: A, B, C; 5 DAH: a, b, c; 10 DAH: m, n, o and 15 DAH: x, y, z).

The invention will now be described in detail in connection with certain preferred and optional embodiments, so that various aspects thereof may be more fully understood and appreciated. The embodiments as described are not limiting or restricting the scope of the invention.

DETAILED DESCRIPTION OF THE INVENTION

As used herein 'Farnesyl pyrophosphate synthase' means and refers to an enzyme that catalyzes formation of farnesyl pyrophosphate.

In an embodiment, the present invention relates to a primer sequence for amplifying farnesyl pyrophosphate synthase having sequence selected from the group consisting of Seq Id. nos. 1-3 and 5-7.

Accordingly, the degenerate primers for amplification of mango cDNA are:

```
for1:
                                              (Seq ID-1)
5'- TKGAYTACAAYGTVCCHGGAGG -3' for2:
                                              (Seq ID-2)
5'- CYCTYGGYTGGYGYATTGAATGG -3', rev:
                                              (Seq ID-3)
5'- YTAYTTYTGCCTCTTRTADATYTT -3'
```

Forward and reverse gene specific primers for amplification of the ends of cDNA by rapid amplification ends (RACE) are as described below:

```
for
                                              (Seq ID-4)
5'- AGTATTCATTGCCACTTCATTGCCAG -3', rev
                                              (Seq ID-5)
5'- ACTTTCATACTCTGCAAACGCACCC -3'
```

Primers corresponding to the terminal regions of the mRNA which are designed for FPPS and for the PCR amplification with mango cDNA as a template represent the following sequences:

```
for
                                              (Seq ID-6)
5'- ATGAGTGATTTGAAGTCCAAGTTCG -3', rev
                                              (Seq ID-7)
5'- CTACTTCTGCCTCTTATATATCTTGG -3'
```

In another embodiment, the present invention discloses an isolated novel nucleotide sequence encoding FPPS derived from mango (NCBI sequence ID: EU 513268).

The complete open reading frame encoding farnesyl pyrophosphate synthase isolated from mango is as shown in FIG. 1.

A cDNA encoding farnesyl pyrophosphate synthase from mango has been isolated and sequenced, and the corresponding amino acid sequence has been deduced. Accordingly, the present invention relates to isolated DNA sequences which code for the expression of farnesyl pyrophosphate synthase, such as the sequence designated SEQ ID No:8 which encodes farnesyl pyrophosphate synthase from mango.

The nucleotide sequence encoding FPPS is useful for enzyme production in an artificial system. This artificially synthesized enzyme can be appropriately mixed with the mango pulp to generate the desired flavor. The nucleotide sequence is also useful for semi-biosynthesis of flavors via various approaches such as enzyme immobilization, single cell culture, etc., as well as to improve other varieties of mango. Mature raw fruits of mango used in the present invention are collected from Dapoli, Deogad and Vengurle regions of Maharashtra.

According to the present invention, the complete open reading frame encoding farnesyl pyrophosphate synthase isolated from mango is as shown in FIG. 1. The degenerate primers of farnesyl pyrophosphate synthase useful for the amplification of the mango cDNA are:

```
for1:
                                              (Seq ID-1)
5'- TKGAYTACAAYGTVCCHGGAGG -3' for2:
                                              (Seq ID-2)
5'- CYCTYGGYTGGYGYATTGAATGG -3', rev:
                                              (Seq ID-3)
5'- YTAYTTYTGCCTCTTRTADATYTT -3'
```

Forward and reverse gene specific primers of farnesyl pyrophosphate synthase for amplification of the ends of cDNA by rapid amplification of cDNA ends (RACE). The gene specific primers useful for the amplification of the ends of mango cDNA are:

```
for
                                              (Seq ID-4)
5'- AGTATTCATTGCCACTTCATTGCCAG -3', rev
                                              (Seq ID-5)
5'- ACTTTCATACTCTGCAAACGCACCC -3'
```

Primers corresponding to the terminal regions of the mRNA which are designed for FPPS and which are used for the PCR amplification with mango cDNA as a template. The terminal primers are:

```
for
                                              (Seq ID-6)
5'- ATGAGTGATTTGAAGTCCAAGTTCG -3', rev
                                              (Seq ID-7)
5'- CTACTTCTGCCTCTTATATATCTTGG -3'
```

In yet another embodiment, the present invention disclose a process for isolating full-length nucleotide sequence encoding farnesyl pyrophosphate synthase from ripe mangoes designated as MiFPPS (JN388975) (*Mangifera indica* farnesyl pyrophosphate synthase). The process comprises the following steps:
i. isolating RNA by CTAB method;
ii. treating total RNA with DNase and carrying out reverse transcription to obtain cDNA;
iii. designing degenerate primers for FPPS based on conserved regions in the nucleotide sequences of farnesyl pyrophosphate synthase reported in the NCBI database;

iv. amplifying cDNA using the degenerate primers of step (ii);
v. designing gene specific primers for FPPS based on the sequence of the fragments obtained in step (iv);
vi. amplifying the ends of the cDNA using gene specific primers of step (v) by Rapid Amplification of cDNA Ends (RACE);
vii. designing primers corresponding to the terminal regions of mRNA based on the alignment of 5' and 3' RACE fragments with the FPPS sequences reported from other plants; and
viii. amplifying mango cDNA using primers obtained in step (vii) by PCR (polymerase chain reaction) using the Expand High Fidelity PCR System (La Roche, Switzerland) to obtain the full length sequence of mango FPPS (MiFPPS).

The process of isolating full-length sequence of farnesyl pyrophosphate synthase (MiFPPS) from ripe mango fruits comprises isolating RNA by CTAB method, treating isolated RNA with DNase and carrying out reverse transcription of the isolated RNA. Based on the conserved regions in the nucleotide sequences of orthologous farnesyl pyrophosphate synthase reported in the NCBI database degenerate primers are designed. These primers are used for the amplification of cDNA prepared from ripe fruits of mango. This is followed by designing gene specific primers based on the sequence of the fragments obtained by amplification over the cDNA. The gene specific primers are used for amplification of the ends of the cDNA by rapid amplification of cDNA ends (RACE). Based on the alignments of the 5' and 3' RACE fragments with the FPPS sequences reported from the other plants, primers corresponding to the terminal regions of the mRNA are designed and are used for obtaining full-length sequence of MiFPPS.

According to the process, after each amplification step, the fragments are eluted from the agarose gel, ligated in a pGEM-T Easy vector and transformed in *E. coli* cells. Positive colonies are identified by colony PCR and the presence of desired insert is confirmed by sequencing. Sequences are aligned and analysed for the presence of uninterrupted reading frame in the MEGA 4.1 software.

The degenerate primers designed in step (iii) of the process for isolating full-length nucleotide sequence encoding FPPS from ripe mangoes are as follows;

```
for1:
                                        (Seq ID-1)
5'- TKGAYTACAAYGTVCCHGGAGG -3', for2:
                                        (Seq ID-2)
5'- CYCTYGGYTGGYGYATTGAATGG -3', rev:
                                        (Seq ID-3)
5'- YTAYTTYTGCCTCTTRTADATYTT -3'.
```

The gene specific primers designed in step (v) of the process of isolating full-length nucleotide sequence encoding FPPS from ripe mangoes are as follows;

```
for
                                        (Seq ID-4)
5'- AGTATTCATTGCCACTTCATTGCCAG -3', rev
                                        (Seq ID-5)
5'- ACTTTCATACTCTGCAAACGCACCC -3'.
```

The terminal primers designed in step (vii) of the process of isolating full-length nucleotide sequence encoding FPPS from ripe mangoes are as follows;

```
for
                                        (Seq ID-6)
5'- ATGAGTGATTTGAAGTCCAAGTTCG -3', rev
                                        (Seq ID-7)
5'- CTACTTCTGCCTCTTATATATCTTGG -3'
```

The complete open reading frame (ORF) of MiFPPS (JN 035296) thus obtained is 1029 base pair long and is flanked by 40 untranslated nucleotides at 5' end up to the first in-frame ATG and 259 nucleotides at the 3' end including the AATAAAA motif between the stop codon and the polyadenylation sequences. The reading frame encodes a protein of 343 amino acids with a calculated molecular weight of 39.5 kD and an isoelectric point of 5.35. When ends of the cDNAs are amplified by RACE, the obtained fragments show sequence similarity to the 5' and 3' ends of full-length FPP synthase genes reported from the other plants. No intervening stop codons are detected upon in silico translation of the DNA sequence constructed from these fragments. These observations suggest that the overlapping 5' and 3' fragments obtained represent the complete open reading frame of the *M. indica* FPP synthase (MiFPPS). The genomic organization of MiFPPS, shows the presence of 11 introns and 12 exons, consistent with that of an *Arabidopsis* FPP synthase gene, the only previous such gene whose genomic structure has been reported (Cunillera et al., 1996). The length of the gene sequence isolated is 331 base pair.

Accordingly, in an assay when isopentenyl pyrophosphate (IPP) with dimethylallyl pyrophosphate (DMAPP) is used as an allylic substrate, the recombinantly expressed MiFPPS produces farnesyl pyrophosphate (FPP) as its major product. It is well-known that during the biogenesis of isopentenyl pyrophosphates higher than GPP, additions of two or more units of IPP to DMAPP occur sequentially. DMAPP condenses with the first molecule of IPP to produce gerenyl pyrophosphate (GPP) which remains enzyme bound (Elitzur et al., 2010) and this is used as an allylic substrate for the sub-sequential addition of another molecule of IPP. Thus, the detection of trace amounts of GPP (1-3% of the total) during the assay with MiFPPS can be hypothesized to be a consequence of a truncated in vitro reaction, as well as attributed to residual *E. coli* enzyme. During the enzymatic reaction catalyzed by prenyltransferases, the participation of divalent metal ions such as $Mg^{2+}$ is necessary for the dissociation of pyrophosphate moiety from the allylic substrate. $Mg^{2+}$ is also required for the binding of the substrate molecules to the enzyme (King and Rilling, 1977). These facts clearly explain the absence of MiFPPS activity in the absence of $MgCl_2$. A few of the FPP synthases reported till now are at least partially active with $Mn^{2+}$ as a cofactor instead of $Mg^{2+}$ (Hemmerlin et al., 2003; Ogura et al., 1985). Strikingly, MiFPPS does not show any activity when $Mn^{2+}$ is used as a divalent metal ion. Since mango fruits contain a more than 600 fold higher concentration of magnesium as compared to manganese (Malik et al., 2004), the lack of activity with $Mn^{2+}$ might be explained as an adaptation of MiFPPS to the higher concentration of $Mg^{2+}$ in the fruits. The absence of activity with the other two divalent cations, $Zn^{2+}$ and $Ca^{2+}$ is consistent with most of the isopentenyl-diphosphate synthases reported till now. The optimum pH of 7.5 observed for MiFPPS is similar to the near-neutral optimal pH observed for FPP synthase from pumpkin fruit (Ogura et al., 1985), *Ricinus communis* (Green and West, 1974) and cotton (Widmaier et al., 1980). At the unripe stage, the pH of the mango fruit pulp is highly acidic and there is a sharp increase in fruit pH during ripening (Yashoda et al., 2006) which could result in increased activity of MiFPPS because of shift of the physiological pH towards the optimal range of MiFPPS. The temperature of mango fruits rises almost up to 40° C. because of increased rate of respiration while ripening (Kumar et al., 1990). This balances the increased activity of MiFPPS due to increased pH.

The present invention further provides three-dimensional structure of MiFPPS using avian FPPS as a template. The avian FPPS shows 50% sequence identity with MiFPPS. Accordingly, homology modeling with the avian FPPS as a template is performed and the quality of the generated model is assessed by a Ramachandran plot, which shows the presence, of 98% residues in the allowed region. All isoprenyl diphosphate synthases which carry out additions of IPP units to allylic substrates show the presence of five conserved regions (I-V). MiFPPS contains all of these regions with regions II and V having the first and second aspartate-rich motifs (FARM and SARM), respectively. The aspartate residues in these regions are involved in binding with the pyrophosphate moiety of substrate through $Mg^{2+}$ bridges (King and Rilling, 1977). The replacement of aspartate residues in these regions with other amino acids results in drastic reduction in enzymatic efficiency (Marrero et al., 1992) (Joly and Edwards, 1993; Song and Poulter, 1994). In the modeled structure of MiFPPS, extension of the carboxylic side chains of these aspartate residues into the substrate binding cleft supports their role in binding the pyrophosphate moieties of the substrate. A stretch of about seven amino acids before FARM forms the chain-length determining (CLD) region of the prenyltransferases, with the amino acids at the fourth and fifth position before FARM deciding the chain-length of the products. If these amino acids are aromatic, their bulky side chains protrude into the activity cavity preventing further chain elongation of the prenyl pyrophosphate product and such enzymes usually synthesize shorter products such as GPP or FPP (Wang and Ohnuma, 1999). On the other hand, in the isoprenyldiphosphate synthases synthesizing longer products, such as geranylgeranyl pyrophosphate (GGPP) synthase, these amino acids are usually smaller (Ohnuma et al., 1996). In the case of MiFPPS, these chain-length determining residues are tyrosine and phenylalanine, and in the modeled structure the side-chain of phenylalanine is observed to protrude into the central cavity supporting the functional characterization of MiFPPS as a farnesyl pyrophosphate synthase. Further, FPPSs are classified into two types based on their chain-length determining mechanisms. In Type I FPPS, two aromatic amino acids in the CLD region are solely responsible for determining the product length and the FARM is constituted by $DDX_2D$. On the other hand, in Type II FPPS, only the 4th amino acid upstream of FARM is aromatic and FARM is formed by $DDX_4D$ (Ohnuma et al., 1997). Based on these reports and the sequence analysis, MiFPPS can be classified as a Type I FPPS.

Profiles the transcripts of MiFPPS in order to get insight into the involvement of MiFPPS in the regulation of sequisterpene biosynthesis is provided herein. The transcripts of MiFPPS are profiled through the four ripening stages of mango from Dapoli, Deogad and Vengurle regions of Maharashtra. The transcript profiling of MiFPPS reveals that the profile is consistent through the ripening process for all three localities. Such consistency suggests a key ripening-related role of the MiFPPS protein. The highest expression is observed at 10 days after harvest DAH stage. This is an important stage in the ripening of mango fruits in which the color turns yellowish and fruit softening begins. In tomato, it has been shown that during ripening, especially, during the color-turning stage (between mature green and red) there is a substantial accumulation of sterols (Chow and Jen, 1978; Whitaker, 1988), which has been hypothesized to play a role in the structural changes, in the cell membrane associated with fruit softening. A similar ripening-related accumulation of sterols has also been reported in apple (Galliard, 1968). Although no reports are available for mango, being a climacteric fruit such an accumulation of sterols during ripening is very likely and can explain the rise, in MiFPPS transcripts at the 10 DAH stage. Secondly, in tobacco the overexpression of yeast FPPS resulted in the increased accumulation not only of sterols, but also of carotenoids (Daudonnet et al., 1997). Considering that the carotenoids are the major components of ripe mango color, a role of MiFPPS in this aspect is also likely. The novel nucleotide sequence encoding FPPS may be used to generate a transgenic variety of mango.

INDUSTRIAL ADVANTAGES

Sesquiterpenes represent one of the important classes of flavor and fragrance chemicals. These chemicals are also nowadays being considered for the biofuel applications. The coding sequence of the enzyme, farnesyl diphosphate synthase, characterized in this study can be used for biotechnological production of the recombinant enzyme which can be further used for the production of sesquiterpenes. The degenerate primers described here have been designed by homology-based approach based on the putative gene sequences reported from the other plants. These primers can thus be used for isolating similar genes from the other plants also.

The novel nucleotide sequences of the present invention can be used for enzyme production in an artificial system and later this artificially synthesized enzyme can be mixed appropriately with any desired food product for generating the desired flavor. The nucleotide sequences can also be used for semi-biosynthesis of flavors via various approaches such as enzyme immobilization, single cell culture, etc., as well as to improve other varieties of mango. Also farnesyl pyrophosphate (FPP), which is the product of FPPS, is a starting material for the synthesis of anticancer drugs (for example, artemisin). The dephosphorylated derivative of FPP, farnesol, as well as the downstream biological product of FPP, sesquiterpenes can be used as fragrance materials to impart floral odor. Farnesol also has the potential to be used as a biofuel component.

REFERENCES CITED IN SPECIFICATION

Adiwilaga, K., Kush, A., 1996. Cloning and characterization of cDNA encoding farnesyl diphosphate synthase from rubber tree (*Hevea brasiliensis*). Plant Molecular Biology 30, 935-946.

Attucci, S., Aitken, S. M., Gulick, P. J., Ibrahim, R. K., 1995. Farnesyl pyrophosphare synthase from white lupin-molecular cloning, expression and purification of the expressed protein Archives of Biochemistry and Biophysics 321, 493-500.

Banyai, W., Kirdmanee, C., Mii, M., Supaibulwatana, K., 2010. Overexpression of farnesyl pyrophosphate synthase (FPS) gene affected artemisinin content and growth of *Artemisia annua* L. Plant Cell Tissue and Organ Culture 103, 255-265.

Breathnach, R., Chambon, P., 1981. Organization and expression of eukaryotic split genes-coding for proteins. Annual Review of Biochemistry 50, 349-383.

Chappell, J., 1995. The biochemistry and molecular biology of isoprenoid metabolism. Plant Physiology 107, 1-6.

Chen, A. J., Kroon, P. A., Poulter, C. D., 1994. Isoprenyl diphosphate synthases-protein-sequence comparison, a phylogenetic tree, and prediction of secondary structure Protein Science 3, 600-607.

Chen, D. H., Ye, H. C., Li, G. F., 2000. Expression of a chimeric farnesyl diphosphate synthase gene in *Artemisia annua* L. transgenic plants via *Agrobacterium tumefaciens*-mediated transformation. Plant Science 155, 179-185.

Chow, E. T. S., Jen, J. J., 1978. Phytosterol biosynthesis in ripening tomatoes. Journal of Food Science 43, 1424-1426.

Clark, B. C., Chamblee, T. S., Iacobucci, G. A., 1987. HPLC isolation of the sesquiterpene hydrocarbon germacrene B from lime peel oil and its characterization as an important flavor impact constituent. Journal of Agricultural and Food Chemistry 35, 514-518.

Closa, M., Vranova, E., Bortolotti, C., Bigler, L., Arro, M., Ferrer, A., Gruissem, W., 2010. The *Arabidopsis thaliana* FPP synthase isozymes have overlapping and specific functions in isoprenoid biosynthesis, and complete loss of FPP synthase activity causes early developmental arrest. Plant Journal 63, 512-525.

Cunillera, N., Arro, M., Delourme, D., Karst, F., Boronat, A., Ferrer, A., 1996. *Arabidopsis thaliana* contains two differentially expressed farnesyl-diphosphate synthase genes. Journal of Biological Chemistry 271, 7774-7780.

Cunillera, N., Boronat, A., Ferrer, A., 1997. The *Arabidopsis thaliana* FPS1 gene generates a novel mRNA that encodes a mitochondrial farnesyl-diphosphate synthase isoform. Journal of Biological Chemistry 272, 15381-15388.

Cunillera, N., Boronat, A., Ferrer, A., 2000. Spatial and temporal patterns of GUS expression directed by 5' regions of the *Arabidopsis thaliana* farnesyl diphosphate synthase genes FPS1 and FPS2. Plant Molecular Biology 44, 747-758.

Daudonnet, S., Karst, F., Tourte, Y., 1997. Expression of the farnesyldiphosphate synthase gene of *Saccharomyces cerevisiae* in tobacco. Molecular Breeding 3, 137-145.

Delourme, D., Lacroute, F., Karst, F., 1994. Cloning of an *Arabidopsis thaliana* cDNA coding for farnesyl diphosphate synthase by functional complementation in yeast Plant Molecular Biology 26, 1867-1873.

Elitzur, T., Vrebalov, J., Giovannoni, J. J., Goldschmidt, E. E., Friedman, H., 2010. The regulation of MADS-box gene expression during ripening of banana and their regulatory interaction with ethylene. Journal of Experimental Botany 61, 1523-1535.

Gaffe, J., Bru, J. P., Causse, M., Vidal, A., Stamitti-Bert, L., Carde, J. P., Gallusci, P., 2000. LEFPSI, a tomato farnesyl pyrophosphate gene highly expressed during early fruit development. Plant Physiology 123, 1351-1362.

Galliard, T., 1968. Aspects of lipid metabolism in higher plants-II. Identification and quantitative analysis of lipids from pulp of pre- and post-climacteric apples. Phytochemistry 7, 1915-1922.

Green, T. R., West, C. A., 1974. Purification and characterization of 2 forms of geranyl transferase from *Ricinus communis*. Biochemistry 13, 4720-4729.

Grunler, J., Ericsson, J., Dallner, G., 1994. Branch-point reactions in the biosynthesis of cholesterol, dolichol, ubiquinone and prenylated proteins. Biochimica Et Biophysica Acta-Lipids and Lipid Metabolism 1212, 259-277.

Han, J. L., Liu, B. Y., Ye, H. C., Wang, H., Li, Z. Q., Li, G. F., 2006. Effects of overexpression of the endogenous farnesyl diphosphate synthase on the artemisinin content in *Artemisia annua* L. Journal of Integrative Plant Biology 48, 482-487.

Hemmerlin, A., Rivera, S. B., Erickson, H. K., Poulter, C. D., 2003. Enzymes encoded by the farnesyl diphosphate synthase gene family in the big sagebrush *Artemisia tridentata* ssp spiciformis. Journal of Biological Chethistry 278, 32132-32140.

Joly, A., Edwards, P. A., 1993. Effect of site-directed mutagenesis of conserved aspartate and arginine residues upon farnesyl diphosphate synthase activity. Journal of Biological Chemistry 268, 26983-26989.

Kim, 0. T., Ahn, J. C., Hwang, S. J., Hwang, B., 2005. Cloning and expression of a farnesyl diphosphate synthase in *Centella asiatica* (L.) urban. Molecules and Cells 19, 294-299.

Kim, 0. T., Bang, K. H., Jung, S. J., Kim, Y. C., Hyun, D. Y., Kim, S. H., Cha, S. W., 2010 Molecular characterization of ginseng farnesyl diphosphate synthase gene and its up-regulation by methyl jasmonate. Biologia Plantarum 54, 47-53.

King, H. L., Rilling, H. C., 1977. Avian liver prenyltransferase-Role of metal in substrate binding and orientation of substrates during catalysis. Biochemistry 16, 3815-3819.

Kumar, S., Patil, B. C., Sinha, S. K., 1990. Cyanide resistant respiration is involved in temperature rise in ripening mangoes. Biochemical and Biophysical Research Communications 168, 818-822.

Kulkarni R S, Chidley H G, Pujari K H, Giri A P and Gupta V S, 2012, Geographic variation in the flavour volatiles of Alphonso mango. Food Chemistry, 130, 58-66

Liao, Z. H., Chen, M., Gong, Y. F., Li, Z. G., Zuo, K. J., Wang, P., Tan, F., Sun, X. F., Tang, K. X., 2006. A new farnesyl diphosphate synthase gene from *Taxus media* Rehder: Cloning, characterization and functional complementation. Journal of Integrative Plant Biology 48, 692-699.

Liu, C., Meng, Y., Hou, S., Chen, X., 1998. Cloning and sequencing of a cDNA encoding farnesyl pyrophosphate synthase from *Gossypium arboreum* and its expression pattern in the developing seeds of *Gossypium hirsutum* cv. "Sumian-6". Acta Botanica Sinica 40, 703-710.

Lovell, S. C., Davis, I. W., Adrendall, W. B., de Bakker, P. I. W., Word, J. M., Prisant, M. G., Richardson, J. S., Richardson, D. C., 2003. Structure validation by C alpha geometry: phi,psi and C beta deviation. Proteins-Structure Function and Genetics 50, 437-450.

Malik, I. O., Babiker, E. E., Yousif, N. E., El Tinay, A. H., 2004. In vitro availability of minerals of some tropical and citrus fruits as influenced by antinutritional factors. Nahrung-Food 48, 65-68.

Manzano, D., Busquets, A., Closa, M., Hoyerova, K., Schaller, H., Kaminek, M., Arro, M., Ferrer, A., 2006. Overexpression of farnesyl diphosphate synthase in *Arabidopsis* mitochondria triggers light-dependent lesion formation and alters cytokinin homeostasis. Plant Molecular Biology 61, 195-213.

Marrero, P. F., Poulter, C. D., Edwards, P. A., 1992. Effects of site-directed mutagenesis of the highly conserved aspartate residues in domain-H of farnesyl diphosphate synthase activity. Journal of Biological Chemistry 267, 21873-21878.

Masferrer, A., Arro, M., Manzano, D., Schaller, H., Fernandez-Busquets, X., Moncalean, P., Fernandez, B., Cunillera, N., Boronat, A., Ferrer, A., 2002. Overexpression of *Arabidopsis thaliana* farnesyl diphosphate synthase (FPS1S) in transgenic *Arabidopsis* induces a cell death/senescence-like response and reduced cytokinin levels. Plant Journal 30, 123-132.

Matsushita, Y., Kang, W., Charlwood, B. V., 1996. Cloning and analysis of a cDNA encoding farnesyl diphosphate synthase from *Artemisia annua*. Gene 172, 207-209.

Ogura, K., Nishino, T., Shinka, T., Seto, S., 1985. Prenyltransferases of pumpkin fruit. Methods in Enzymology 110, 167-171.

Ohnuma, S., Hirooka, K., Ohto, C., Nishino, T., 1997. Conversion from archaeal geranylgeranyl diphosphate synthase to farnesyl diphosphate synthase—Two amino acids before the first aspartate-rich motif solely determine eukaryotic farnesyl diphosphate synthase activity. Journal of Biological Chemistry 272, 5192-5198.

Ohnuma, S., Narita, K., Nakazawa, T., Ishida, C., Takeuchi, Y., Ohto, C., Nishino, T., 1996. A role of the amino acid residue located on the fifth position before the first aspartate-rich motif of farnesyl diphosphate synthase on determination of the final product. Journal of Biological Chemistry 271, 30748-30754.

Pan, Z. Q., Herickhoff, L., Backhaus, R. A., 1996. Cloning, characterization, and heterologous expression of cDNAs for farnesyl diphosphate synthase from the guayule rubber plant reveals that this prenyltransferase occurs in rubber particles. Archives of Biochemistry and Biophysics 332, 196-204.

Pandit, S. S., Kulkarni, R. S., Giri, A. P., Koellner, T. G., Degenhardt, J., Gershenzon, J., Gupta, V. S., 2010. Expression profiling of various genes during the fruit development and ripening of mango. Plant Physiology and Biochemistry (Paris) 48, 426-433.

Pandit, S. S., Mitra, S. S., Giri, A. P., Gupta, V. S., 2007. A quick method for isolating RNA from raw and ripe fleshy fruits as well as for co-isolating DNA and RNA from polysaccharide- and polyphenol-rich leaf tissues. Journal of Plant Biology 50, 60-64.

Sallaud, C., Rontein, D., Onillon, S., Jabes, F., Duffe, P., Giacalone, C., Thoraval, S., Escoffier, C., Herbette, G., Leonhardt, N., Causse, M., Tissier, A., 2009. A novel pathway for sesquiterpene biosynthesis from Z,Z-farnesyl pyrophosphate in the wild tomato *Solanum habrochaites*. Plant Cell 21, 301-317.

Sanmiya, K., Iwasaki, T., Matsuoka, M., Miyao, M., Yamamoto, N., 1997. Cloning of a cDNA that encodes farnesyl diphosphate synthase and the blue-light-induced expression of the corresponding gene in the leaves of rice plants. Biochimica Et Biophysica Acta-Gene. Structure and Expression 1350, 240-246.

Schmidt, A., Gershenzon, J., 2007. Cloning and characterization of isoprenyl diphosphate synthases with farnesyl diphosphate and geranylgeranyl diphosphate synthase activity from Norway spruce (*Picea abies*) and their relation to induced oleoresin formation. Phytochemistry 68, 2649-2659.

Seigler, D. S., 1998. Plant secondary metabolism. Kluwer Academic Publishers.

Sippl, M. J., 1993. Recognition of errors in 3-dimensional structures of proteins. Proteins-Structure Function and Genetics 17, 355-362.

Song, L. S., Poulter, C. D., 1994. Yeast farnesyl-diphosphate synthase—site-directed mutagenesis of residues in highly conserved prenyltransferase domain-I and domain-II. Proceedings of the National Academy of Sciences of the United States of America 91, 3044-3048.

Szkopinska, A., Plochocka, D., 2005. Farnesyl diphosphate synthase; regulation of product specificity. Acta Biochimica Polonica 52, 45-55.

Tamura, K., Dudley, J., Nei, M., Kumar, S., 2007. MEGA4: Molecular evolutionary genetics analysis (MEGA) software version 4.0. Molecular Biology and Evolution 24, 1596-1599.

Tarshis, L. C., Yan, M. J., Poulter, C. D., Sacchettini, J. C., 1994. Crystal-structure of recombinant farnesyl diphosphate synthase at 2.6-angstrom resolution. Biochemistry 33, 10871-10877.

Vandermoten, S., Haubruge, E., Cusson, M., 2009. New insights into short-chain prenyltransferases: structural features, evolutionary history and potential for selective inhibition. Cellular and Molecular Life Sciences 66, 3685-3695.

Wang, K., Ohnuma, S., 1999. Chain-length determination mechanism of isoprenyl diphosphate synthases and implications for molecular evolution. Trends in Biochemical Sciences 24, 445-451.

Wang, P., Liao, Z. H., Guo, L., Li, W. C., Chen, M., Pi, Y., Gong, Y. F., Sun, X. F., Tang, K. X., 2004. Cloning, and functional analysis of a cDNA encoding *Ginkgo biloba* farnesyl diphosphate synthase. Molecules and Cells 18, 150-156.

Weinstein, J. D., Branchaud, R., Beale, S. I., Bement, W. J., Sinclair, P. R., 1986. Biosynthesis of the farnesyl moiety of heme a from exogenous mevalonic acid by cultured chick liver-cells. Archives of Biochemistry and Biophysics 245, 44-50.

Whitaker, B. D., 1988. Changes in the steryl lipid-content and composition of tomato fruit during ripening. Phytochemistry 27, 3411-3416.

Widmaier, R., Howe, J., Heinstein, P., 1980. Prenyltransferase from *Gossypium hirsutum*. Archives of Biochemistry and Biophysics 200, 609-616.

Wiederstein, M., Sippl, M. J., 2007. ProSA-web: interactive web service for the recognition of errors in three-dimensional structures of proteins. Nucleic Acids Research 35, W407-W410.

Xiang, L., Zhao, K. G., Chen, L. Q., 2010. Molecular cloning and expression of *Chimonanthus praecox* farnesyl pyrophosphate synthase gene and its possible involvement in the biosynthesis of floral volatile sesquiterpenoids. Plant Physiology and Biochemistry 48, 845-850.

Yashoda, H. M., Prabha, T. N., Tharanathan, R. N., 2006. Mango ripening: changes in cell wall constituents in relation to textural softening. Journal of the Science of Food and Agriculture 86, 713-721.

Zhao, Y. J., Ye, H. C., Li, G. F., Chen, D. H., Liu, Y., 2003. Cloning and enzymology analysis of farnesyl pyrophosphate synthase gene from a superior strain of *Artemisia annua* L. Chinese Science Bulletin 48, 63-67.

EXAMPLES

The following examples are given by way of illustration of a simple portable type charcoal kiln for wood, sticks and leaves, in actual practice and should not be constructed to limit the scope of the present invention.

Example 1

Plant Material

Mature raw fruits of mango were collected from the orchards of Konkan Krishi Vidyapeeth at Dapoli (N17°45' E73°11') and Deogad (N16°31' E73°20') and from a private orchard at Vengurle (N15°51' E73°39'). For each of the three localities, fruits were collected from four plants. After harvesting, fruits were put in hay, carried to the laboratory and allowed to ripen at ambient temperature. At intervals of five days, fruits were cut, immediately frozen in the liquid nitrogen and stored at −80° C. until use, giving rise to four measurement points during ripening: 0, 5, 10 and 15 DAH (days after harvest) from each of the three localities.

Example 2

RNA Isolation and cDNA Synthesis

RNA was isolated by CTAB method (Pandit et al., 2007). After treating total RNA with DNase, reverse transcription was carried out over 1 μg of total RNA using Enhanced Avian RT First Strand Synthesis Kit (Sigma, St. Louis, Mo., USA). The cDNA so obtained was used to amplify the MiFPPS transcript fragments using degenerate primers and later to measure the MiFPPS transcript abundance through real time PCR.

Example 3

Isolation of Full-Length MiFPPS

Based on the conserved regions in the nucleotide sequences of farnesyl pyrophosphate synthase genes reported in the NCBI database, degenerate primers (for1: 5'-TKGAYTACAAYGTVCCHGGAGG-3' (SEQ ID NO:1), for2: 5'-CYCTYGGYTGGYGYATTGAATGG-3' (SEQ ID NO:2), rev: 5'-YTAYTTYTGCCTCTTRTADATYTT-3' (SEQ ID NO:3)) were designed. These primers were used for the amplification over the cDNA prepared from ripe fruits of mango. The gene specific primers (for 5'-AGTAT-TCATTGCCACTTCATTGCCAG-3' (SEQ ID NO:4), rev 5'-ACTTTCATACTCTGCAAACGCACCC-3' (SEQ ID NO:5)) designed based on the sequence of the fragments obtained were used for amplification of the ends of the cDNA by rapid amplification of cDNA ends (RACE) using a SMART™ RACE cDNA Amplification Kit (Clontech, Palo Alto, Calif., USA). Based on the alignments of the 5' and 3' RACE fragments with the FPPS sequences reported from other plants, primers corresponding to the terminal regions of the mRNA were designed (for 5'-ATGAGT-GATTTGAAGTCCAAGTTCG-3' (SEQ ID NO:6), rev 5'-CTACTTCTGCCTCTTATATATCTTGG-3' (SEQ ID NO:7)) and were used for the PCR with mango cDNA as a template. The genomic fragment MiFPPS was isolated by carrying out PCR using the above-mentioned terminal primers over the genomic DNA isolated from mango leaves by the method described earlier (Pandit et al., 2007). After each step of PCR mentioned above, the fragments were eluted from the agarose gel, ligated in pGEM-T Easy vector (Promega, Madison, Wis., USA) and the ligation reactions were transformed in E. coli cells (Top 10, Invitrogen, Carlsbad, Calif., USA). Positive colonies were identified by colony PCR and the presence of desired insert was confirmed by sequencing. Sequences were aligned and analyzed for the presence of an uninterrupted reading frame in the MEGA 4.1 software (Tamura et al., 2007).

The complete open reading frame of 1029 bp was flanked by 40 untranslated nucleotides at 5' end up to the first in-frame ATG and 259 nucleotides at the 3' end including the AATAAAA motif between the stop codon and the polyadenylation sequences. The reading frame encoded a protein of 342 amino acids with a calculated molecular weight of 39.5 kD and an isoelectric point of 5.35. The in silico translated amino acid sequence of MiFPPS showed the highest homology with FPPS from *Panax ginseng* (86% identity) (Kim et al., 2010), *Centellaasiatica* (85% identity) (Kim et al., 2005) and *Heveabrasiliensis* (84% identity) (Adiwilaga and Kush, 1996). Alignment of the *Mangifera indica* FPPS (MiFPPS) with the FPPS sequences from other plants revealed the presence of five regions which are conserved among prenyltransferases (Chen et al., 1994). Out of these, regions II and V contained the first aspartate rich motif (FARM, between amino acids 93 and 97) and the second aspartate rich motif (SARM, between amino acids 232 and 236), respectively which are essential for substrate binding and catalysis (FIG. 2a).

To obtain information about the genomic organization of MiFPPS, PCR was carried out on the genomic DNA of mango using the terminal primers. The resulting fragment of about 3.8 kb was cloned and its sequence was determined by primer walking. The genomic sequence of MiFPPS showed the presence of 11 introns having a total size of 2717 base pairs (FIG. 2b). The shortest and the longest introns had sizes of 87 base pairs and 897 base pairs, respectively. Almost all the introns followed the "GT-AG" rule (Breathnach and Chambon, 1981): the introns began with GT at the 5' ends and ended with AG at the 3' end. The length of the gene sequence isolated was 331 base pair.

Example 4

Expression Cloning and Recombinant Expression in E. coli

The full length sequence of mango FPPS (MiFPPS) was amplified using the Expand High Fidelity PCR System (La Roche, Basel, Switzerland) with the terminal primers described above. cDNA prepared from the ripe fruit was used as template and the resulting fragment was cloned in the pEXP5-CT/TOPO expression vector (Invitrogen). The ligation reaction was transformed in the E. coli strain TOP10F' (Invitrogen) and the transformants were selected on the LB-agar media containing 100 μg/ml carbenicillin. After confirming the correct orientation of the insert and the presence of an uninterrupted reading frame, the recombinant plasmids were transformed in the BL21 (DE3) pLysS cells (Invitrogen). Five ml of starter culture grown at 18° C. for 48 hours was used as inoculum for the expression in 100 ml LB medium with the Overnight Express Autoinduction System 1 (Novagen, Madison, Wis., USA). Cultures were grown for 24 hours at 18° C. and the pellet obtained after centrifugation was resuspended in the buffer containing 25 mM MOPSO (pH 7.2), 10 mM $MgCl_2$ and 10% (v/v) glycerol and lysed by sonication. The $(his)_6$-tagged recombinant protein was purified by passing the cleared lysate through Ni-NTA resin (Qiagen, Hilden, Germany) following the manufacturer's instructions. Elution was carried out with a buffer containing 250 mM imidazole, 25 mM MOPSO (pH 7.2), 10 mM $MgCl_2$ and 10% (v/v) glycerol. Both crude lysate and the purified protein were checked for the presence of the recombinant protein by SDS-PAGE.

Before actual expression, the deduced amino acid sequence of MiFPPS was analyzed on the PROSO server to predict the solubility of the recombinantly expressed protein in *E. coli*. The prediction that MiFPPS would be soluble upon heterologous expression with the probability of 0.507 proved correct and a substantial amount of recombinant protein was obtained in the soluble fraction upon expression. Purification of the crude soluble fraction through a Ni-NTA agarose matrix yielded a protein of the expected size.

Example 5

Assay for Enzymatic Activity

In vitro assay for determining the activity of MiFPPS was carried out in a final volume of 200 µl containing about 0.5 µg of the purified protein, 25 mM MOPSO (pH 7.0), 10% (v/v) glycerol, 2 mM DTT, 10 mM $MgCl_2$ and 67 µM of each DMAPP and IPP (Echelon Biosciences, Salt Lake City, USA). In a qualitative test to find the allylic specificity of MiFPPS towards substrate, 67 µM GPP was used as an allylic substrate instead of DMAPP in the separate reaction having the same composition as mentioned above. For the optimum pH determination of the recombinant enzyme, assays were performed in 25 mM MOPSO (pH 6 and 6.5), 25 mM HEPES (pH 7 and 7.5) or 25 mM TRIS (pH 8, 8.5 and 9) containing the other required components as mentioned above. The assays carried out for determining the optimum $Mg^{2+}$ concentration, contained varied concentrations of $MgCl_2$ along with the other required components as mentioned above. After overnight incubation, the assay reactions were deproteinized by washing with equal volume of chloroform and used directly for LC-MS/MS analysis.

Consistent with the sequence-based characterization of the isolated cDNA as a FPPS, recombinantly expressed MiFPPS produced FPP as its major product. MiFPPS was confirmed to produce E,E-FPP as its main product along with about 1-3% of GPP. The very minute amounts of GPP and FPP detected in the assays with the protein expressed from an empty vector can be attributed to the activity of the enzymes from *E. coli* (FIG. 3). Neither FPP nor GPP were detected in the enzyme assays with the boiled protein, without protein and without substrates.

The optimum temperature for the activity of recombinant enzyme was found to be 25° C. and more than 75% of the optimum activity was retained at 15° C. and 20° C.; however, the activity was sharply reduced beyond 25° C. (FIG. 4). When the activity of MiFPPS was assayed at varying pH, maximum FPP production was observed at pH 7.5 with retention of more than 80% activity between pH 7 and 9; however, only about 10% of the optimum activity was detected below pH 7. The enzyme also required $Mg^{2+}$ as a divalent metal ion cofactor for its activity. The optimum $MgCl_2$ concentration was found to be 0.3 mM with 67 µM DMAPP and IPP and the enzyme possessed more than 75% of the maximum activity at 1 mM $MgCl_2$ after which the activity declined slowly. Strikingly, MiFPPS specifically required $Mg^{2+}$ for catalysis and was found to be inactive with other divalent metal ions such as $Mn^{2+}$, $Zn^{2+}$ and $Ca^{2+}$ in the concentration range of 0.5-12 mM. To test whether the enzyme shows any specificity towards allylic substrates, GPP was added as the allylic substrate instead of DMAPP. It was observed that MiFPPS was able to condense GPP and IPP to produce FPP.

Example 6

LC-MS/MS Analysis

Analysis of isoprenoid pyrophosphates was performed on an Agilent 1200 HPLC system (Agilent Technologies, Santa Clara, Calif., USA) coupled to an API 3200 triple quadrupole mass spectrometer (Applied Biosystems, Foster City, Calif., USA). The column used was an Agilent ZORBAX Extended C-18; 1.8 µm, 50×4.6 mm (Agilent Technologies). Mobile phase consisted of 5 mM ammonium bicarbonate in water as solvent A and acetonitrile as solvent B, flow rate was set at 0.8 ml/min and column temperature at 20° C. Separation was achieved using a gradient starting at 0% B increasing to 10% B in 2 min, 64% B in 12 min and 100% B in 2 min keeping it at 100% B for 1 min followed by a change to 0% B in 1 min and keeping it for another 5 min before the next injection. Injection volume for samples and standards was 10 µl. The mass spectrometer was used in the negative electrospray ionization mode. Optimal settings were determined using standards purchased from Sigma-Aldrich. Ion source gas 1 and 2 were set at 60 and 70 psi having a temperature of 700° C., curtain gas was set at 30 psi and collision gas at 7 psi. Ion spray voltage was maintained at −4200 V. Monitored MRM transitions were m/z 312.9/79 for GPP, m/z 380.9/79 for FPP and m/z 449/79 for GGPP. Data analysis was performed using Analyst Software 1.5 Build 3385 (Applied Biosystems).

Example 7

Homology Modeling

The three-dimensional structure of MiFPPS was determined on the CPH model 3.0 server. Avian FPPS (PDB ID IFPS) (Tarshis et al., 1994), which shows 50% sequence identity with. MiFPPS, was used as a template. Ramchandran plot assessment of the structure was carried out on the RAMPAGE server (Lovell et al., 2003). Further quality parameters of the generated model were assessed on a web-based program, ProSA (Sippl, 1993; Wiederstein and Sippl, 2007).

The quality of the generated model was assessed by a Ramachandran plot, which showed the presence of 98% residues in the allowed region. Further evaluation of the structure by ProSA-web yielded a Z-score of −9.46 and negative energy values for all the residues in the energy plot. Root mean square deviation for superimposition of the modeled structure of MiFPPS with the template (avian FPPS) was 0.61 Å. All of these assessments point towards the good quality of the model generated for MiFPPS.

Figure 5A:
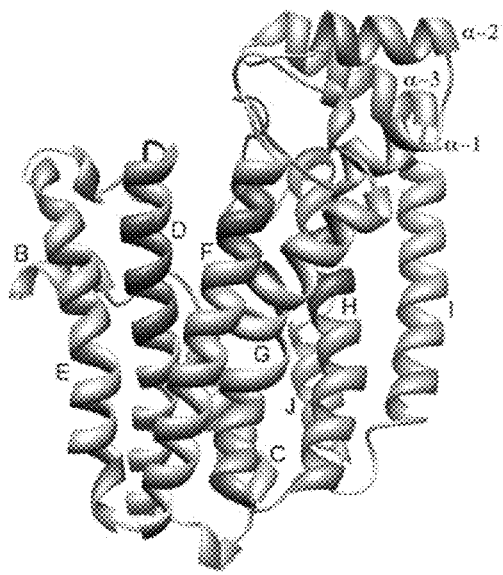
Figure 5B:
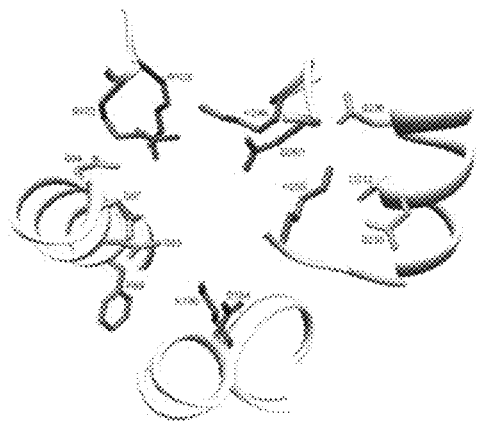

The avian FPPS has 10 helices (A-J). While the structure of MiFPPS at the region corresponding to helix A of avian FPPS could not be determined because of low sequence identity of this region, the other nine helices (B-J) were evident and surrounded the central reaction cavity (FIG. 5a). All the five regions conserved in isoprenyl diphosphate synthases lined the substrate binding cavity. The FARM and SARM regions were present on the opposite walls of the cavity on the D and H helix, respectively. The carboxylate side chains of all six aspartate residues in FARM and SARM were extended into the substrate binding cleft. The side-chain of the phenylalanine residue present before FARM, known to be involved in the chain-length determination of the product, also protruded into the active-site cavity (FIG. 5b).

Example 8 qRT-PCR

Quantitative PCR was performed with Brilliant SYBR Green QPCR Master Mix (Stratagene, La Jolla, Calif., USA). Mango elongation factor 1α (MiEF1α) transcript was used for normalization (Pandit et al., 2010). Primers used for amplifying a fragment of MiFPPS transcript were: for 5'-TGGGAAAGCAGATCCAGCCTGTGT-3' (SEQ ID NO: 19) and rev 5'-TGCACTTTCATACTCTGCAAACGCA-3' (SEQ ID NO: 20). For MiEF1α the primers used were same as described earlier (Pandit et al., 2010). For both MiFPPS and MiEF1α at least three amplicons were sequenced to confirm the primer specificity. Transcript abundance was quantified with a Mx3000P Real Time PCR Thermocycler (Stratagene, La Jolla, Calif., USA) using a program with 45 cycles of 95° C. for 30 seconds, 63° C. for 30 seconds and 72° C. for 30 seconds, followed by a melting curve analysis of transcripts. The relative transcript abundance of MiFPPS for the raw stage (0 DAH) from Dapoli was considered 1 and the fold difference for the rest of the tissues was calculated. Each measurement was repeated with four independent biological replicates, each of which was represented by at least two technical replicates.

When the ripening stages were compared to each other, the level of expression of MiFPPS for all three localities was similar for the raw (0 days after harvest) and 5 DAH fruits. Such consistency suggested a key ripening-related role of the MiFPPS protein. The highest expression was observed at 10 DAH stage. About 6.6, 7.6 and 16 fold increase in the expression was observed at the 10 DAH stage as compared to the 0 DAH stage for Vengurle, Deogad and Dapoli, respectively (FIG. 6). This is an important stage in the ripening of mango fruits in which the color turns yellowish and fruit softening begins. Although the transcripts were present in the higher amounts in the ripe (15 DAH) stage than the raw stage, the levels were reduced by about half in comparison with 10 DAH, at all three localities. When the localities were compared to each other for the expression level of MiFPPS, at 0 and 15 DAH the highest expression was depicted by the Deogad fruits; whereas, at 5 and 10 DAH, the maximum expression was shown by the Dapoli fruits (FIG. 6). Though the MiFPPS expression pattern through ripening was similar for all three localities, only the correlation between Dapoli and Vengurle was significant at $p<0.05$

Example 9

Statistical Analysis

All the statistical analyses were carried out using the Statview software, version 5.0 (SAS Institute Inc., Cary, N.C., USA). ANOVA was carried out to assess the significance of the difference in the relative transcript levels of MiFPPS between the ripening stages and the difference in the relative activity of the recombinant enzyme at different reaction conditions, by Fisher's LSD at $p<0.05$. For every two cultivation localities, the relative transcript abundance profiles of MiFPPS through the ripening stages were correlated.

We claim:

1. A population of degenerate primers for amplifying farnesyl pyrophosphate synthase, wherein the population has a sequence selected from the group consisting of SEQ ID NO: 1, SEQ ID NO:2, and SEQ ID NO:3.

2. The population of claim 1 where the population comprises SEQ ID NO:1 and SEQ ID NO:3.

3. The population of claim 1 where the population comprises SEQ ID NO:2 and SEQ ID NO:3.

4. The population of claim 1 where the population comprises SEQ ID NO:1.

5. The population of claim 1 where the population comprises SEQ ID NO:2.

6. The population of claim 1 where the population comprises SEQ ID NO:3.

* * * * *